(12) United States Patent
Genet et al.

(10) Patent No.: US 6,638,321 B1
(45) Date of Patent: *Oct. 28, 2003

(54) CATIONIC OXIDATION BASES, THEIR USE FOR OXIDATION DYEING OF KERATIN FIBRES, DYEING COMPOSITIONS AND DYEING METHODS

(75) Inventors: Alain Genet, Aulay-sous-Bois (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,663

(22) PCT Filed: Jul. 13, 1998

(86) PCT No.: PCT/FR98/01535

§ 371 (c)(1),
(2), (4) Date: Jun. 7, 1999

(87) PCT Pub. No.: WO99/03836

PCT Pub. Date: Jan. 28, 1999

(30) Foreign Application Priority Data

Jul. 16, 1997 (FR) .............................................. 97 09028

(51) Int. Cl.$^7$ ........................ C07D 233/54; A61K 7/13
(52) U.S. Cl. ...................... 8/407; 8/409; 8/410; 8/416; 8/423; 8/426; 8/513; 8/655; 564/290; 564/282; 564/287; 548/314.4; 548/335.5; 548/346.1; 548/300.1; 548/356.1; 548/375.1
(58) Field of Search ........................... 8/407, 409, 410, 8/416, 423, 426, 573, 655; 564/290, 287, 282; 548/314.4, 335.5, 346.1, 300.1, 356.1, 375.1

(56) References Cited

U.S. PATENT DOCUMENTS

| | | | |
|---|---|---|---|
| 3,100,739 A | 8/1963 | Kaiser et al. .................. | 8/426 |
| 3,442,895 A | 5/1969 | Bugaut et al. ................ | 544/156 |
| 3,467,483 A | 9/1969 | Bugaut et al. .................. | 8/426 |
| 3,528,972 A | 9/1970 | Kalopissis et al. ........... | 544/156 |
| 3,622,629 A * | 11/1971 | Lugosy ....................... | 564/287 |
| 4,581,370 A * | 4/1986 | Diamond et al. ......... | 548/335.5 |
| 4,888,025 A * | 12/1989 | Bugaut et al. ................ | 8/405 |
| 4,975,092 A | 12/1990 | Chan et al. .................... | 8/408 |
| 5,135,543 A | 8/1992 | Chan et al. .................... | 8/405 |
| 5,137,538 A | 8/1992 | Madrange et al. ............. | 8/410 |
| 5,139,532 A | 8/1992 | Chan et al. .................... | 8/405 |
| 5,344,464 A | 9/1994 | Madrange et al. ............. | 8/410 |
| 5,514,188 A | 5/1996 | Cotteret et al. ................ | 8/412 |
| 5,735,908 A | 4/1998 | Cotteret et al. ................ | 8/410 |
| 5,735,910 A | 4/1998 | Lagrange et al. .............. | 8/415 |

FOREIGN PATENT DOCUMENTS

| | | |
|---|---|---|
| BE | 616 439 | 10/1962 |
| DE | 1 135 589 | 8/1962 |
| DE | 1 292 784 | 4/1969 |
| EP | 0 360 644 | 3/1990 |
| EP | 0 544 400 | 6/1993 |
| EP | 0 634 164 | 1/1995 |
| EP | 0 673 641 | 9/1995 |
| EP | 0 673 926 | 9/1995 |
| EP | 0 728 463 | 8/1996 |
| FR | 1 391 675 | 12/1965 |
| FR | 2 213 968 | 8/1974 |
| FR | 2 217 390 | 9/1974 |
| FR | 2 586 913 | 3/1987 |
| FR | 2 630 438 | 10/1989 |
| GB | 1 211 801 | 11/1970 |
| GB | 1364952 * | 8/1974 |
| GB | 2 018 453 | 10/1979 |
| WO | WO 95/01772 | 1/1995 |
| WO | WO 95/12585 | 5/1995 |
| WO | WO 95/15144 | 6/1995 |
| WO | WO 97/39727 | 10/1997 |

OTHER PUBLICATIONS

C. Tomaier, "Phenols, Anilines: Bases Coupleurs a Azote Quaternaire Extra–Nucleaire", Bibliographie No. 307, Jun. 1996, pp. 2–28.
C. Tomaier, "Bis–Quaternaires en Cosmetique", Bibliographie No. 317, Feb. 1997, pp. 2–35.
L.K.J. Tong et al., "The Mechanism of Dye Formation in Color Photography. VII. Intermediate Bases in the Deamination of Quinonediimines", Journal of American Chemical Scoeity, vol. 82, No. 8, Apr. 1960, pp. 1988–1996.
English language Derwent Abstract of EP 0 728 463, 8/96.
English language Derwent Abstract of FR 2 213 968, 9/74.
English language Derwent Abstract of FR 2 217 390, 10/74.
English language Derwent Abstract of FR 2 586 924, 3/87.
English language Derwent Abstract of FR 2 630 438, 10/89.

\* cited by examiner

*Primary Examiner*—Margaret Einsmann
(74) *Attorney, Agent, or Firm*—Finnegan Henderson Farabow Garrett & Dunner LLP

(57) ABSTRACT

The invention relates to novel monobenzene oxidation bases containing at least one cationic group Z, Z being chosen from aliphatic chains containing at least one quaternized unsaturated ring, to their use for the oxidation dyeing of keratin fibers, to dye compositions containing them and to oxidation dyeing processes using them.

36 Claims, No Drawings

CATIONIC OXIDATION BASES, THEIR USE FOR OXIDATION DYEING OF KERATIN FIBRES, DYEING COMPOSITIONS AND DYEING METHODS

The invention relates to novel monobenzene oxidation bases containing at least one cationic group Z, Z being chosen from aliphatic chains containing at least one quaternized unsaturated ring, to their use for the oxidation dyeing of keratin fibres, to dye compositions containing them and to oxidation dyeing processes using them.

It is known practice to dye keratin fibres, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

It has already been proposed, in particular in U.S. Pat. No. 5,139,532, to use certain cationic para-phenylenediamine derivatives, i.e. more precisely, para-phenylenediamines in which one of the amino groups is monosubstituted with a quaternized aliphatic chain, for the oxidation dyeing of keratin fibres in strong shades which are redder than those usually obtained using standard para-phenylenediamines, i.e. compounds containing no cationic groups. However, the use of the para-phenylenediamines described in that prior patent does not make it possible to obtain a wide range of colours and, furthermore, the colorations obtained are not always entirely satisfactory from the point of view of their resistance with respect to the various forms of attack to which the hair may be subjected (action of light, perspiration, shampoo, etc.).

Now, the Applicant has just discovered, entirely surprisingly and unexpectedly, that certain novel monobenzene oxidation bases of formula (I) defined below, containing at least one cationic group Z, Z being chosen from aliphatic chains containing at least one quaternized unsaturated ring, are not only suitable for use as oxidation dye precursors, but also allow dye compositions to be obtained which lead to strong colorations, in a wide range of colours, and which have excellent properties of resistance to the various treatments to which keratin fibres may be subjected. Lastly, these compositions prove to be readily synthesizable.

These discoveries form the basis of the present invention.

A first subject of the invention is thus novel compounds of formula (I) below, and the addition salts thereof with an acid:

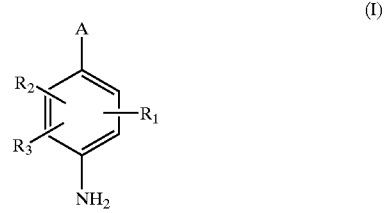

in which:

$R_1$, $R_2$ and $R_3$, which may be identical or different, represent a hydrogen atom; a halogen atom; a group Z; a ($C_1$–$C_6$)alkylcarbonyl radical; an amino($C_1$–$C_6$) alkylcarbonyl radical; an N—Z—amino($C_1$–$C_6$) alkylcarbonyl radical; an N—($C_1$–$C_6$)alkylamino ($C_1$–$C_6$)alkylcarbonyl radical; an N,N-di($C_1$–$C_6$) alkylamino($C_1$–$C_6$)alkylcarbonyl radical; an amino ($C_1$–$C_6$ alkylcarbonyl($C_1$–$C_6$)alkyl radical; an N—Z-amino($C_{C6}$)alkylcarbonyl($C_1$–$C_6$)alkyl radical; an N—($C_1$–$C_1$)alkylamino($C_1$–$C_6$)alkylcarbonyl-($C_1$–$C_6$) alkyl radical; an N,N-di($C_1$–$C_6$)alkylamino($C_1$–$C_6$) alkylcarbonyl($C_1$–$C_6$)alkyl radical; a carboxyl radical; an ($C_1$–$C_6$)alkylcarboxyl radical; a $C_1$–$C_6$ alkylsulphonyl radical; an aminosulphonyl radical; an N—Z-amino-sulphonyl radical; a $C_1$–$C_6$ N—alkylaminosulphonyl radical; an N,N-di($C_1$–$C_6$) alkylaminosulphonyl radical; a $C_1$–$C_6$ aminosulphonylalkyl radical; a $C_1$–$C_6$ N—Z-amino-sulphonylalkyl radical; an N—($C_1$–$C_6$)alkylaminosulphonyl($C_1$–$C_6$) alkyl radical; an N,N-di($C_1$–$C_6$)alkylaminosulphonyl ($C_1$–$C_6$)alkyl radical; a carbamyl radical; an N—($C_1$–$C_6$)alkylcarbamyl radical; an N,N-di($C_1$—$_6$) alkylcarbamyl radical; a carbamyl($C_1$–$C_6$)alkyl radical; an N—($C_1$–$C_6$)alkylcarbamyl($C_1$–$C_6$)alkyl radical; an N,N-di($C_{1–6}$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_2$–$C_6$ trifluoroalkyl radical; a cyano radical; a group $OR_6$ or $SR_6$; an amino group protected with a ($C_1$–$C_6$)alkylcarbonyl, ($C_1$–$C_6$) alkylcarboxyl, trifluoro($C_1$–$C_6$)alkylcarbonyl, amino ($C_1$–$C_6$)alkylcarbonyl, N—Z-amino($C_1$–$C_6$) alkylcarbonyl, N—($C_1$–$C_6$)alkylamino($C_1$–$C_6$) alkylcarbonyl, N,N-di($C_1$–$C_6$)alkylamino($C_1$–$C_6$) alkylcarbonyl, ($C_1$–$C_{16}$)alkylcarboxyl, carbamyl, N—($C_1$–$C_6$)alkylcarbamyl, N,N-di($C_1$–$C_6$) alkylcarbamyl, $C_1$–$C_6$ alkylsulphonyl, aminosulphonyl, N—Z-aminosulphonyl, $C_1$–$C_6$ N-alkylaminosulphonyl, N,N-di($C_1$–$C_6$)alkylamino-sulphonyl, thiocarbamyl or formyl radical, or with a group Z; or a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, carbamyl, N—($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$) alkylcarboxyl and thiocarbamyl radicals, or with a group Z;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a $(C_1-C_6)$alkoxy$(C_1-C_6)$alkyl radical; an aryl radical; a benzyl radical; a carboxy$(C_1-C_6)$alkyl radical; a $(C_1-C_6)$alkylcarboxy$(C_1-C_6)$alkyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a $C_1-C_6$ trifluoroalkyl radical; a $C_1-C_6$ aminosulphonylalkyl radical; a $C_1-C_6$ N—Z-aminosulphonylalkyl radical; an N—$(C_1-C)$alkylaminosulphonyl$(C_1-C_6)$alkyl radical; an N,N-di$(C_{11}-C_6)$alkylaminosulphonyl$(C_1-C_6)$alkyl radical; a $(C_1-C_6)$alkylsulphinyl$(C_1-C_6)$alkyl radical; a $(C_1-C_1)$alkylsulphonyl$(C_1-C_6)$alkyl radical; a $(C_1-C_6)$alkylcarbonyl$(C_1-C_6)$alkyl radical; a $C_1-C_6$ aminoalkyl radical; a $C_1-C_6$ aminoalkyl radical in which the amine is substituted with one or two identical or different radicals chosen from $C_1-C_6$ alkyl, $C_1-C_6$ monohydroxyalkyl, $C_2-C_6$ polyhydroxyalkyl, $(C_1-C_6)$ alkylcarbonyl, formyl, trifluoro$(C_1-C_6)$alkylcarbonyl, $(C_1-C_6)$alkylcarboxyl, carbamyl, N—$(C_1-C_6)$alkylcarbamyl, N,N-di$(C_1-C_6)$alkylcarbamyl, thiocarbamyl and $C_1-C_6$ alkylsulphonyl radicals, and the group Z;

A represents a group —$NR_4R_5$ or a hydroxyl radical;

$R_4$ and $R_5$, which may be identical or different, represent a hydrogen atom; a group Z; a $C_1-C_6$ alkyl radical; a $C_1-C_6$ monohydroxyalkyl radical; a $C_2-C_6$ polyhydroxyalkyl radical; a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a $C_1-C_6$ trifluoroalkyl radical; a $C_1-C_6$ sulphoalkyl radical; a $(C_1-C_6)$alkylcarboxy$(C_1-C_6)$alkyl radical; a $(C_1-C_6)$alkylsulphinyl$(C_1-C_6)$alkyl radical; a $C_1-C_6$ aminosulphonylalkyl radical; a $C_1-C_6$ N—Z-aminosulphonylalkyl radical; an N—$(C_1-C_6)$alkylaminosulphonyl$(C_1-C_6)$alkyl radical; an N,N-di$(C_1-C_6)$alkylaminosulphonyl$(C_1-C_6)$)alkyl radical; a $(C_1-C_6)$alkylcarbonyl$(C_1-C_6)$alkyl radical; a $C_1-C_6$ aminoalkyl radical; a $C_1-C_6$ aminoalkyl radical in which the amine is substituted with one or two identical or different radicals chosen from $C_1-C_6$ alkyl, $C_1-C_6$ monohydroxyalkyl, $C_2-C_6$ polyhydroxyalkyl, $(C_1-C_6)$ alkylcarbonyl, carbamyl, N—$(C_1-C_6)$alkylcarbamyl, N,N-di$(C_1-C_6)$alkylcarbamyl, $C_1-C_6$ alkylsulphonyl, formyl, trifluoro$(C_1-C_6)$alkylcarbonyl, $(C_1-C_6)$ alkylcarboxyl and thiocarbamyl radicals, or with a group Z;

Z is chosen from the unsaturated cationic groups of formulae (II) and (III) below, and the saturated cationic groups of formula (IV) below:

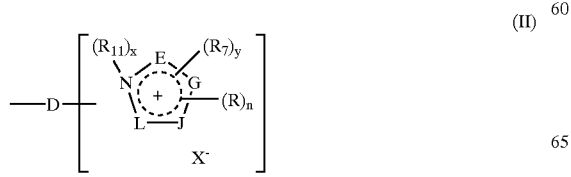
(II)

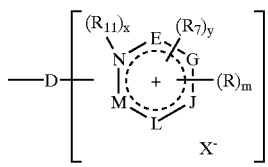
(III)

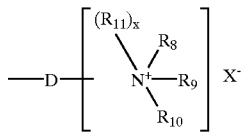
(IV)

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1-C_6$ alkoxy radicals, and which can bear one or more ketone functions;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a group Z, a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a cyano$(C_1-C_6)$alkyl radical, a $C_1-C_6$ alkoxy radical, a tri$(C_1-C_6)$alkylsilane$(C_1-C_6)$alkyl radical, an amido radical, an aldehydo radical, a carboxyl radical, a $(C_1-C_6)$alkylcarbonyl radical, a thio radical, a $C_1-C_6$ thioalkyl radical, a $C_1-C_6$ alkylthio radical, an amino radical, an amino radical protected with a $(C_1-C_6)$ alkylcarbonyl, carbamyl or $C_1-C_6$ alkylsulphonyl radical; a group NHR" or NR"R'" in which R" and R'", which may be identical or different, represent a $C_1-C_6$ alkyl radical, a $C_1-C_6$ monohydroxyalkyl radical or a $Cc_2-C_6$ polyhydroxyalkyl radical;

$R_7$ represents a $C_1-C_6$ alkyl radical, a $C_1-C_6$ monohydroxyalkyl radical, a $C_2-C_6$ polyhydroxyalkyl radical, a cyano$(C_1-C_6)$alkyl radical, a tri$(C_1-C_6)$alkylsilane$(C_1-C_6)$alkyl radical, a $(C_1-C_6)$alkoxy$(C_1-C_6)$alkyl radical, a carbamyl$(C_1-C_6)$alkyl radical, a $(C_1-C_6)$ alkylcarboxy$(C_1-C_6)$alkyl radical, a benzyl radical or a group Z of formula (II), (III) or (IV) as defined above;

$R_8$, $R_9$ and $R_{10}$, which may be identical or different, represent a $C_1-C_6$ alkyl radical, a $C_1-C_6$ monohydroxyalkyl radical, a $C_2-C_6$ polyhydroxyalkyl radical, a $(C_1-C_6)$alkoxy$(C_1-C_6)$alkyl radical, a cyano$(C_1-C_6)$ alkyl radical, an aryl radical, a benzyl radical, a $C_1-C_6$ amidoalkyl radical, a tri$(C_1-C_6)$alkylsilane$(C_1-C_6)$ alkyl radical or a $C_1-C_6$ aminoalkyl radical in which the amine is protected with a $(C_1-C_6)$alkylcarbonyl, carbamyl or $C_1-C_6$ alkylsulphonyl radical; two of the radicalism $R_8$, $R_9$ and $R_{10}$ can together also form, with the nitrogen atom to which they are attached, a saturated 5- or 6-membered carbon ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$) alkylsilane($C_1$–$C_6$)alkyl radical, an amido radical, an aldehydo radical, a carboxyl radical, a keto($C_1$–$C_6$) alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical; one of the radicals $R_8$, $R_9$ and $R_{10}$ can also represent a second group Z which is identical to or different from the first group Z;

$R_{11}$ represents a $C_1$–$C_1$ alkyl radical; a $C_1$–$C_6$ monohydroxyalkyl radical; a $C_2$–$C_1$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl ($C_1$–$C_6$)alkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

x and y are integers equal to 0 or 1; with the following conditions:

in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical R, is borne by the nitrogen atom of the unsaturated ring; or alternatively
2) when at least one of the ring members E, G, J and L represents a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M represents a divalent atom and when the radical $R_7$ is borne by the nitrogen atom of the unsaturated ring;

in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the said saturated ring;

X⁻ prepresents a monovalent or divalent anion and is preferably chosen from a halogen atom such as chlorine, bromine, fluorine or iodine, a hydroxide, a hydrogenosulphate or a $C_1$–$C_6$ alkyl sulphate such as, for example, a methyl sulphate or an ethyl sulphate; it being understood:
that the number of unsaturated cationic groups Z of formula (II) or (III) is at least equal to 1;

that when A represents a group —$NR_4R_5$, in which $R_4$ or $R_5$ represents a group Z in which the linker arm D represents an alkyl chain containing a ketone function, then the said ketone function is not directly attached to the nitrogen atom of the group —$NR_4R_5$;

and with the exclusion of 4-amino-3-methyl-N-ethyl-N-β-(1-pyridinium)ethylaniline chloride.

As mentioned above, the colorations obtained with the oxidation dye composition in accordance with the invention are strong and produce a wide range of colours. They moreover have excellent properties of resistance to the action of various external agents (light, bad weather, washing, permanent-waving, perspiration, friction). These properties are particularly noteworthy, in particular as regards the resistance of the colorations obtained to the action of light.

In formula (I) above, the alkyl and alkoxy radicals can be linear or branched.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

Among the compounds of formula (I) above, mention may be made in particular of:

1-[2-(4-aminophenylamino)ethyl]-3-methyl-3H-imidazol-1-ium bromide;

1-[3-(2,5-diaminophenoxy)propyl]-3-methyl-3H-imidazol-1-ium chloride;

3-[3-(4-aminophenylamino)propyl]-1-methyl-3H-imidazol-1-ium chloride;

3-[3-(4-amino-3-methylphenylamino)propyl]-1-methyl-3H-imidazol-1-ium chloride;

3-[3-(4-amino-2-methylphenylamino)propyl]-1-methyl-3H-imidazol-1-ium chloride;

3-[3-(4-amino-2-fluorophenylamino)propyl]-1-methyl-3H-imidazol-1-ium chloride monohydrate;

3-[3-(4-amino-2-cyanophenylamino)propyl]-1-methyl-3H-imidazol-1-ium chloride;

1-[2-(4-amino-2-methoxyphenylamino)ethyl]-3-methyl-3H-imidazol-1-ium chloride;

1-(5-amino-2-hydroxybenzyl)-3-methyl-3H-imidazol-1-ium chloride;

1-(5-amino-2-hydroxybenzyl)-2-methyl-2H-pyrazol-1-ium chloride;

1-[2-(2,5-diaminophenyl)ethyl]-3-methyl-3H-imidazol-1-ium chloride;

3-[2-(2,5-diaminophenyl)ethyl]-1-methyl-3H-imidazol-1-ium chloride;

1-{2-[(4-aminophenyl)ethylamino]ethyl}-3-methyl-3H-imidazol-1-ium chloride;

N,N-bis[2-(3-methyl-3H-imidazol-1-ium)ethyl]-4-aminoaniline dichloride;

3-[2-(4-aminophenylamino)butyl]-1-methyl-3H-imidazol-1-ium chloride;

1-{[5-amino-2-(2-hydroxyethylamino)phenylcarbamoyl]methyl}-3-methyl-3H-imidazol-1-ium chloride;

4-[2-(2,5-diaminophenoxy)ethyl]-1,3-dimethyl-3H-imidazol-1-ium bromide;

2-(2,5-diaminophenoxymethyl)-1,3-dimethyl-3H-imidazol-1-ium chloride;

4-[3-(4-aminophenylamino)propyl]-1,3-dimethyl-3H-imidazol-1-ium chloride;

4-[3-(4-amino-3-methylphenylamino)propyl]-1,3-dimethyl-3H-imidazol-1-ium chloride;

4-[(2,5-diaminophenylcarbamoyl)methyl]-1,3-dimethyl-3H-imidazol-1-ium chloride;

4-{2-[2-(2-amino-5-hydroxyphenyl)acetylamino]ethyl}-1,3-dimethyl-3H-imidazol-1-ium chloride;

4-[(5-amino-2-hydroxybenzylcarbamoyl)methyl]-1,3-dimethyl-3H-imidazol-1-ium chloride;

and the addition salts thereof with an acid.

The compounds of formula (I) in accordance with the invention can be readily obtained according to methods that are well known in the state of the art:

either by reduction of the corresponding cationic nitro compounds (cationic para-nitroanilines or cationic para-nitrophenols), or by reduction of the corresponding cationic nitroso compounds (obtained, for example, by nitrosation of a tertiary aniline or of a corresponding phenol), or by reduction of the corresponding cationic azo compounds (reductive cleavage).

This reduction step (production of a primary aromatic amine) which gives the synthesized compound its nature as an oxidizable compound (oxidation base), which may or may not be followed by a salification, is generally, for convenience, the final step of the synthesis.

This reduction can take place earlier in the sequence of reactions leading to the preparation of the compounds of formula (I), and according to well-known processes it is then necessary to "protect" the primary amine created (for example by an acetylation, benzenesulphonation, etc. step), then carry out the desired substitution(s) or modification(s) (including quaternization) and end by "deprotecting" (generally in acidic medium) the amine function.

Similarly, the phenolic function can be protected according to well-known processes with a benzyl radical ("deprotection" by catalytic reduction) or with an acetyl or mesyl radical ("deprotection" in acidic medium).

When the synthesis is complete, the compounds of formula (I) in accordance with the invention can, if necessary, be recovered by methods which are well known in the state of the art, such as crystallization or distillation.

Another subject of the invention is the use of the compounds of formula (I) in accordance with the invention as oxidation bases for the oxidation dyeing of keratin fibres, and in of particular human keratin fibres such as the hair.

The invention also relates to a composition for the oxidation dyeing of keratin fibres, and in particular of human keratin fibres such as the hair, characterized in that it comprises, as an oxidation base, in a medium which is suitable for dyeing, at least one compound of formula (I) in accordance with the invention.

The compound(s) of formula (I) in accordance with the invention preferably represent(s) from 0.0005 to 12% by weight approximately relative to the total weight of the dye composition, and even more preferably from 0.005 to 6% by weight approximately relative to this weight.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

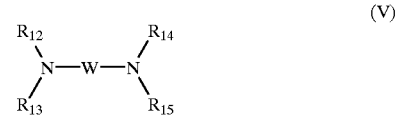

(V)

in which W is a propylene residue optionally substituted with a hydroxyl group or a $C_1$–$C_6$ alkyl radical; $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The dye composition in accordance with the invention can also contain, in addition to the dyes defined above, at least one additional oxidation base which can be chosen from the oxidation bases conventionally used in oxidation dyeing and among which mention may be made in particular of para-phenylenedi-amines other than the compounds of formula (I) in accordance with the invention, bis(phenyl)alkylenediamines, para-aminophenols other than the compounds of formula (I) in accordance with the invention, ortho-aminophenols and heterocyclic bases.

Among the para-phenylenediamines which can be mentioned more particularly, for example, are para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl) para-phenylenediamine, N,N-bis(β-hydroxyethyl)para-phenylenediamine, 4-amino-N-(β-methoxyethyl)aniline and the para-phenylenediamines described in French patent application FR 2,630,438, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine and N,N'-bis (ethyl)-N,N'-bis(4-amino-3'-methylphenyl) ethylenediamine, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino- 2-methoxymethylphenol, 4-amino-2-aminomethylphenol and 4-amino-2-(β-hydroxyethylaminomethyl)phenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof; inorganic or organic thickeners, antioxidants, penetration agents, sequestering agents, fragrances, buffers, dispersing agents, conditioners such as, for example, silicones, film-forming agents, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention without, however, limiting its scope.

PREPARATION EXAMPLES

Preparation Example 1

Synthesis of 1-[2-(4-Amino-phenylamino)ethyl]-3-methyl-3H-imidazol-1-ium Dihydrochloride Monobromide

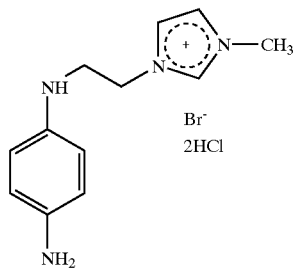

a) Preparation of 3-Methyl-1-[2-(4-nitrophenylamino)ethyl]-3H-imidazol-1-ium Bromide A suspension of 49.0 g (0.2 mol) of (2-bromoethyl)(4-nitrophenyl)amine and of 19.8 g (0.24 mol) of 1-methyl-1H-imidazole in 200 ml of toluene was prepared. The mixture was heated at the reflux point of the toluene with stirring for 4 hours, filtered while hot and reimpasted twice in ethyl acetate and then in absolute ethanol.

After drying at 40° C. under vacuum, pale yellow crystals (62.3 g) of 3-methyl-1-[2-(4-nitrophenylamino)ethyl]-3H-imidazol-1-ium bromide melting at 214° C. (Kofler) were obtained, the elemental analysis of which, calculated for $C_{12}H_{15}N_4O_2Br$, was:

| %          | C     | H    | N     | O    | Br    |
| ---------- | ----- | ---- | ----- | ---- | ----- |
| Calculated | 44.05 | 4.62 | 17.12 | 9.78 | 24.42 |
| Found      | 44.14 | 4.57 | 17.03 | 9.78 | 24.37 | b) Reduction of 3-Methyl-1-[2-(4-nitrophenylamino)ethyl]-3H-imidazol-1-ium Bromide A mixture of 50 ml of 96° ethanol, 5 ml of water, 25 g of finely powdered zinc and 0.5 g of ammonium chloride was heated to the reflux point of the alcohol. 16.4 g (0.05 mol) of 3-methyl-1-[2-(4-nitrophenylamino)ethyl]-3H-imidazol-1-ium bromide obtained in the above step were added portionwise so as to maintain the reflux without heating. The reaction was exothermic.

At the end of the addition, the reflux was maintained for an additional 10 minutes.

The mixture was filtered while hot while pouring into 22 ml of approximately 5N absolute hydrochloric ethanol (ice-cold).

The crystallized precipitate was filtered off, washed with absolute ethanol and dried under vacuum at 40° C. over potassium hydroxide.

After recrystallization from a mixture of water and ethanol at reflux, 10.4 g of white crystals were obtained, melting at 195–200° C. (Kofler) and whose structure was in accordance by $^1$H NMR.

Preparation Example 2

Synthesis of 1-[3-(2,5-Diaminophenoxy)propyl]-3-methyl-3H-imidazol-1-ium Dihydrochloride Monochloride

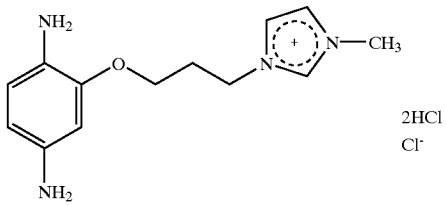

a) Preparation of N-[2-(3Chloropropoxy)-4-nitrophenyl]acetamide

A mixture of 98.1 g (0.5 mol) of N-[2-hydroxy-4-nitrophenyl)acetamide and 69.2 g (0.5 mol) of potassium carbonate in 500ml of dimethylformamide was heated to 50° C. with stirring, 113.0 g (1 mol) of 1,3-dichloropropane were then added and heating was continued at 50° C. for one hour.

The reaction mixture was poured into 4 liters of ice-cold water and the crystallized precipitate was filtered off, reimpasted in water and then in isopropyl alcohol and dried under vacuum at 40° C. over phosphorus pentoxide.

113.5 g of beige-coloured crystals were obtained, which, after purification by recrystallization from refluxing isopropyl acetate, melted at 121° C.

The elemental analysis was in accordance with that calculated for $C_{11}H_{23}N_2O_4Cl$.

b) Preparation of 1-[3-(2-Acetylamino-5-nitrophenoxy)propyl]-3-methyl-3H-imidazol-1-ium Chloride The procedure described above for Example 1, step a) was used.

Starting with 27.2 g (0.1 mol) of N-[2-(3-chloropropoxy)-4-nitrophenyl]acetamide obtained in the above step and 9.9 g (0.12 mol) of 1-methyl-1H-imidazole in 120 ml of toluene, pale yellow crystals (21.5 g) of 1-[3-(2-acetylamino-5-nitrophenoxy)propyl]-3-methyl-3H-imidazol-1-ium chloride melting at 227° C. (Kofler) were obtained, the elemental analysis of which, calculated for $C_{15}H_{19}N_4O_4Cl$, was:

| %          | C     | H    | N     | O     | Cl   |
| ---------- | ----- | ---- | ----- | ----- | ---- |
| Calculated | 50.78 | 5.40 | 15.79 | 18.04 | 9.99 |
| Found      | 50.69 | 5.36 | 15.74 | 18.23 | 9.79 | c) Reduction of 1-[3-(2-Acetylamino-5-nitrophenoxy)propyl]-3-methyl-3H-imidazol-1-ium Chloride The reduction was carried out according to the procedure described for Example 1, step b).

Starting with 21.3 g (0.06 mol) of 1-[3-(2-acetylamino-5-nitrophenoxy)propyl]-3-methyl-3H-imidazol-1-ium chloride and after filtration and evaporation to dryness under reduced pressure, 19.0 g of a brown oil of 1-[3-(2-acetylamino-5-aminophenoxy)propyl]-3-methyl-3H-imidazol-1-ium chloride were obtained.

d) Deacetylation of 1-[3-(2-Acetylamino-5-amino-phenoxy)propyl]-3-methyl-3H-imidazol-1-ium Chloride The 1-[3-(2-acetylamino-5-aminophenoxy)propyl]-3-methyl-3H-imidazol-1-ium chloride obtained in the above step (19.0 g) was dissolved, at room temperature and with stirring, in 90 ml of approximately 5N absolute hydrochloric ethanol.

After half an hour, a white crystalline precipitate appeared.

The suspension was heated to the reflux point of the alcohol for one hour.

The crude product was cooled, filtered off, washed with absolute ethanol and dried at 50° C. under vacuum and over potassium hydroxide.

14.9 g of off-white crystals melting at 216–220° C. (Kofler) were obtained, the elemental analysis of which, calculated for $C_{13}H_2N_4OCl_3$, was:

| %          | C     | H    | N     | O    | Cl    |
|------------|-------|------|-------|------|-------|
| Calculated | 43.90 | 5.95 | 15.75 | 4.50 | 29.90 |
| Found      | 43.83 | 6.01 | 15.62 | 5.09 | 29.90 |

Preparation Example 3

Synthesis of 3-[3-(4-Amino-phenylamino)propyl]-1-methyl-3H-imidazol-1-ium Dihydrochloride Monochloride

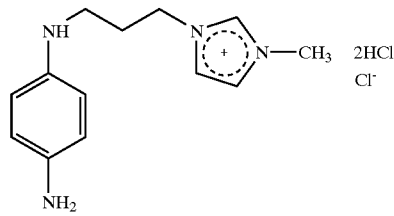

a) Preparation of (3-Imidazol-1-ylproyl)-(4-nitrophenyl) amine

A mixture of 28.2 g (0.2 mol) of 1-fluoro-4-nitrobenzene, 31.3 g (0.25 mol) of 3-imidazol-1-ylpropylamine and 34.8 ml of triethylamine in 30 ml of 1,2-dimethoxyethane was heated for half an hour with stirring. The mixture was poured into 1.5 liters of ice-cold water and the crystalline precipitate was filtered off, reimpasted in water and then in isopropyl alcohol and dried under vacuum at 40° C. over phosphorus pentoxide. Yellow crystals (36.6 g) which, after purification by recrystallization from refluxing 96° ethanol, melted at 124° C., were obtained, the elemental analysis of which, calculated for $C_{12}H_{14}N_4O_2$, was:

| %          | C     | H    | N     | O     |
|------------|-------|------|-------|-------|
| Calculated | 58.53 | 5.73 | 22.75 | 12.99 |
| Found      | 58.17 | 5.75 | 22.67 | 13.45 | b) Quaternization of (3-Imidazol-1-ylpropyl)-(4-nitrophenyl)amine 30.4 g (0.123 mol) of (3-imidazol-1-ylpropyl)-(4-nitrophenyl)amine obtained in the above step and 12.9 ml of dimethyl sulphate were suspended in 600 ml of ethyl acetate and left stirring for 2 hours at room temperature.

The crystalline precipitate was filtered off, washed several times with ethyl acetate, reimpasted in the minimum amount of absolute ethanol and dried under vacuum at 50° C.

37.6 g of yellow crystals melting at 74° C. (Kofler) were obtained, the elemental analysis of which, calculated for $C_{14}H_{20}N_4O_6S$, was:

| %          | C     | H    | N     | O     | S    |
|------------|-------|------|-------|-------|------|
| Calculated | 45.15 | 5.41 | 15.04 | 25.78 | 8.61 |
| Found      | 44.85 | 5.50 | 14.91 | 25.97 | 8.49 | c) Reduction of 1-Methyl-3-[3-(4-nitrophenylamino)propyl]-3H-imidazol-1-ium Methyl Sulphate The reduction was carried out according to the procedure described for Example 1, step b).

Starting with 33.5 g (0.09 mol) of 1-methyl-3-[3-(4-nitrophenylamino)propyl]-3H-imidazol-1-ium methyl sulphate obtained above in the previous step, and after heating in approximately 5N absolute hydrochloric ethanol in order to complete the anion exchange, 18.7 g of white crystals melting with decomposition at 184–190° C. (Kofler) were obtained, the elemental analysis of which, calculated for $C_{13}H_{21}N_4Cl_3 \cdot \frac{1}{3}H_2O$, was:

| %          | C     | H    | N     | O    | Cl    |
|------------|-------|------|-------|------|-------|
| Calculated | 45.17 | 6.32 | 16.21 | 1.54 | 30.77 |
| Found      | 44.98 | 6.22 | 16.05 | 1.57 | 30.78 |

Preparation Example 4

Synthesis of 3-[3-(4-Amino-3-methylphenylamino)propyl]-1-methyl-3H-imidazol-1-ium Monochloride Dihydrochloride

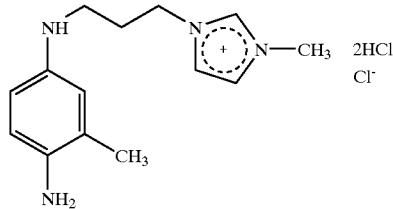

a) Preparation of (3-Imidazol-1-ylpropyl)-(3-methyl-4-nitrophenyl)amine

A mixture of 31.2 g (0.2 mol) of 4-fluoro-2-methyl-1-nitrobenzene, 37.5 g (0.3 mol) of 3-imidazol-1-ylpropylamine and 34.8 ml (0.25 mol) of triethylamine in 30 ml of 1,2-dimethoxyethane was heated with stirring for 3 hours on a boiling water bath.

The mixture was poured into 0.5 l of ice-cold water and the crystalline precipitate was filtered off, reimpasted in water and then in isopropyl alcohol and dried under vacuum at 40° C. over phosphorus pentoxide.

After purification by recrystallization from refluxing 96° ethanol, 17.0 g of orange-yellow crystals melting at 133° C. (Kofler) were obtained, the elemental analysis of which, calculated for $C_{13}H_{16}N_4O_2$, was:

| %          | C     | H    | N     | O     |
|------------|-------|------|-------|-------|
| Calculated | 59.99 | 6.20 | 21.52 | 12.29 |
| Found      | 59.55 | 6.22 | 21.43 | 12.88 | b) Preparation of 1-Methyl-3-[3-(3-methyl-4-nitrophenylamino)propyl]-3H-imidazol-1-ium Methyl Sulphate Quaternization of 16.5 g (0.063 mol) of (3-imidazol-1-ylpropyl)-(3-methyl-4-nitrophenyl)amine obtained above in the previous step, dissolved in 165 ml of ethyl acetate, was carried out by adding 6.7 ml (0.07 mol) of dimethyl sulphate with stirring for one hour at room temperature.

20.8 g of a yellow oil of 1-methyl-3-(3-(3-methyl-4-nitrophenylamino)propyl]-3H-imidazol-1-ium methyl sulphate were obtained.

c) Reduction of 1-Methyl-3-[3-(3-methyl-4-nitrophenylamino)propyl]-3H-imidazol-1-ium Methyl Sulphate The reduction was carried out according to the procedure described above for Example 1, step b).

Starting with 20.0 g (0.051 mol) of 1-methyl-3-[3-(3-methyl-4-nitrophenylamino)propyl]-3H-imidazol-1-ium methyl sulphate obtained above in the previous step, and after heating in approximately 5N absolute hydrochloric ethanol in order to complete the anion exchange, 12.5 g of white crystals melting at 210–220° C. (Kofler) were obtained, the elemental analysis of which, calculated for $C_{14}H_{23}N_4Cl_3 \cdot \frac{1}{2}H_2O$, was:

| % | C | H | N | O | Cl |
|---|---|---|---|---|---|
| Calculated | 46.36 | 6.67 | 15.45 | 2.21 | 29.32 |
| Found | 46.21 | 6.40 | 15.33 | 2.37 | 29.69 |

Preparation Example 5

Synthesis of 3-[3-(4-Amino-2-methylphenylamino)propyl]-1-methyl-3H-imidazol-1-ium Monochloride Dihydrochloride

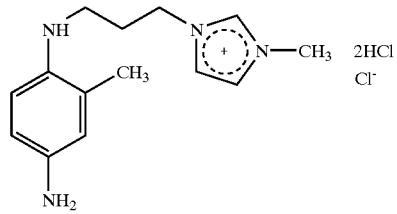

a) Preparation of (3-Imidazol-1-ylpropyl)-(2-methyl-4-nitrophenyl)amine

The procedure described for Example 4, step a) is used.

Starting with 31.2 g (0.2 mol) of 1-fluoro-2-methyl-4-nitrobenzene and 37.5 g (0.3 mol) of 3-imidazol-1-ylpropylamine, and after purification by recrystallization from refluxing 96° C. ethanol, 23.0 g of orange-yellow crystals melting at 163° C. (Kofler) were obtained, the elemental analysis of which, calculated for $C_{13}H_{16}N_4O_2 \cdot \frac{1}{4}H_2O$, was:

| % | C | H | N | O |
|---|---|---|---|---|
| Calculated | 58.97 | 6.28 | 21.16 | 13.59 |
| Found | 59.10 | 6.22 | 21.09 | 12.85 | b) Preparation of 1-Methyl-3-[3-(2-methyl-4-nitrophenylamino)propyl]-3H-imidazol-1-ium Methyl Sulphate The procedure described for Example 4, step b) is used.

Starting with 22.5 g (0.086 mol) of (3-imidazol-1-ylpropyl)-(2-methyl-4-nitrophenyl)amine obtained in the previous step and 9.0 ml (0.095 mol) of methyl sulphate, 19.5 g of yellow crystals of 1-methyl-3-[3-(2-methyl-4-nitrophenylamino)propyl]-3H-imidazol-1-ium methyl sulphate melting at 70° C. (Kofler) were obtained, the elemental analysis of which, calculated for $C_{14}H_{19}N_4O_2$, was:

| % | C | H | N | O | S |
|---|---|---|---|---|---|
| Calculated | 46.62 | 5.74 | 14.50 | 24.84 | 8.30 |
| Found | 46.66 | 5.80 | 14.50 | 24.90 | 8.27 | c) Reduction of 1-Methyl-3-[3-(2-methyl-4-nitrophenylamino)propyl]-3H-imidazol-1-ium Methyl Sulphate The reduction is carried out according to the procedure described for Example 1, step b).

Starting with 19.0 g (0.05 mol) of 1-methyl-3-[3-(2-methyl-4-nitrophenylamino)propyl]-3H-imidazol-1-ium methyl sulphate, and after heating in approximately 5N absolute hydrochloric ethanol in order to complete the anion exchange, 14.6 g of white crystals melting at 255–260° C. (Kofler) were obtained, the elemental analysis of which, calculated for $C_{14}H_{23}N_4Cl_3 \cdot \frac{1}{2}H_2O$, was:

| % | C | H | N | O | Cl |
|---|---|---|---|---|---|
| Calculated | 46.36 | 6.67 | 15.45 | 2.21 | 29.32 |
| Found | 45.84 | 6.63 | 15.35 | 2.09 | 29.67 |

Preparation Example 6

Synthesis of 3-[3-(4-Amino-2-fluorophenylamino)propyl]-1-methyl-3H-imidazol-1-iummonochloride Dihydrochloride Monohydrate

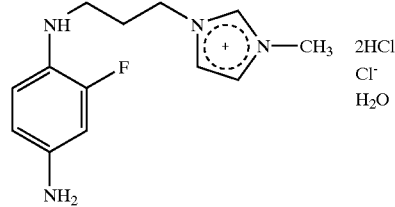

a) Preparation of (2-Fluoro-4-nitrophenyl)-(3-imidazol-1-ylpropyl)amine

The procedure described above for Example 4, step a) is used.

Starting with 31.8 g (0.2 mol) of 1,2-difluoro-4-nitrobenzene and 37.5 g (0.3 mol) of 3-imidazol-1-ylpropylamine, and after purification by recrystallization from refluxing 96° C. ethanol, 36.0 g of orange-yellow crystals melting at 144° C. (Kofler) were obtained, the elemental analysis of which, calculated for $C_{12}H_{13}N_4O_2F$, was:

| % | C | H | N | O | F |
|---|---|---|---|---|---|
| Calculated | 54.54 | 4.96 | 21.20 | 12.11 | 7.19 |
| Found | 54.25 | 4.99 | 21.14 | — | 6.97 | b) Preparation of 3-[3-(2-Fluoro-4-nitropheriylamino) propyl]-1-methyl-3H-imidazol-1-ium Methyl Sulphate The procedure described for Example 4, step b) is used.

Starting with 36.0 g (0.136 mol) of (2-fluoro-4-nitrophenyl)-(3-imidazol-1-ylpropyl)amine obtained in the previous step and 14.3 ml (0.15 mol) of methyl sulphate, 46.0 g of yellow crystals of 3-[3-(2-fluoro-4-nitrophenylamino)propyl]-1-methyl-3H-imidazol-1-ium methyl sulphate melting with decomposition at 110° C. (Kofler) were obtained, the elemental analysis of which, calculated for $C_{14}H_{19}N_4O_6SF$, was:

| % | C | H | N | O | S | F |
|---|---|---|---|---|---|---|
| Calculated | 43.07 | 4.91 | 14.35 | 24.59 | 4.87 | 8.21 |
| Found | 43.00 | 5.00 | 14.37 | — | 4.87 | 8.12 | c) Reduction of 3-[3-(2-Fluoro-4-nitrophenylamino) propyl]-1-methyl-3H-imidazol-1-ium Methyl Sulphate The reduction was carried out according to the procedure described above for Example 1, step b).

Starting with 41.0 g (0.105 mol) of 3-[3-(2-fluoro-4-nitrophenylamino)propyl]-1-methyl-3H-imidazol-1-ium methyl sulphate, and after heating in approximately 5N absolute hydrochloric ethanol in order to complete the anion exchange, 19.0 g of white crystals melting with decomposition at 165–170° C. (Kofler) were obtained, the elemental analysis of which, calculated for $C_{13}H_{20}N_4Cl_3F \cdot H_2O$, was:

| % | C | H | N | O | Cl | F |
|---|---|---|---|---|---|---|
| Calculated | 41.56 | 5.90 | 14.91 | 4.26 | 28.31 | 5.06 |
| Found | 41.59 | 5.41 | 14.88 | — | 29.13 | 5.32 |

Preparation Example 7

Synthesis of 3-[3-(4-Amino-2-cyanophenylamino) propyl]-1-methyl-3H-imidazol-1-ium Monochloride Hydrochloride

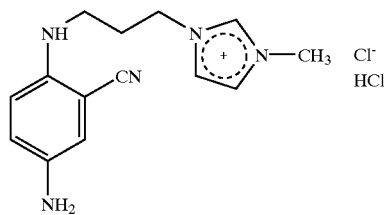

a) Preparation of 2-(3-Imidazol-1-ylpropylamino)-5-nitrobenzonitrile

The procedure described for Example 4, step a) was used, but using N-methylpyrrolidone instead of 1,2-dimethoxyethane.

Starting with 36.5 g (0.2 mol) of 2-chloro-5-nitrobenzonitrile and 31.3 g (0.25 mol) of 3-imidazol-1-ylpropylamine, and after purification by recrystallization from refluxing at 96 ° ethanol, 28.2 g of yellow crystals melting at 177° C. (Kofler) were obtained, the elemental analysis of which, calculated for $C_{13}H_{13}N_5O_2$, was:

| % | C | H | N | O |
|---|---|---|---|---|
| Calculated | 57.56 | 4.83 | 25.82 | 11.80 |
| Found | 57.69 | 4.86 | 25.65 | 11.94 | b) Preparation of 3-[3-(2Cyano-4-nitrophenylamino) propyl]-1-methyl-3H-imidazol-1-ium Methyl Sulphate The procedure described for Example 4, step b) was used.

Starting with 27.7 g (0.102 mol) of 2-(3-imidazol-1-ylpropylamino)-5-nitrobenzonitrile obtained in the previous step and 10.8 ml (0.114 mol) of methyl sulphate, and after purification by recrystallization from absolute ethanol, 30.0 g of yellow crystals of 3-[3-(2-cyano-4-nitrophenylamino) propyl]1-methyl-3H-imidazol-1-ium methyl sulphate melting at 110–115° C. (Kofler) were obtained, the elemental analysis of which, calculated for $C_{15}H_{19}N_5O_6S$, was:

| % | C | H | N | O | S |
|---|---|---|---|---|---|
| Calculated | 45.34 | 4.82 | 17.62 | 24.16 | 8.07 |
| Found | 45.31 | 4.82 | 17.73 | 24.21 | 8.15 | c) Reduction of 3-[3-(2Cyano-4-nitrophenylamino)propyl]-1-methyl-3H-imidazol-1-ium Methyl Sulphate The reduction is carried out according to the procedure described above for Example 1, step b).

Starting with 25.0 g (0.063 mol) of 3-[3-(2-cyano-4-nitrophenylamino)propyl]-1-methyl-3H-imidazol-1-ium methyl sulphate, and after heating in approximately 5N absolute hydrochloric ethanol in order to complete the anion exchange, 16.2 g of white crystals melting at 220° C. (Kofler) were obtained, the $^1$H NMR analysis of which was in accordance with the expected product (non-salified NH).

Preparation Example 8

Synthesis of 1-[2-(4-Amino-2-methoxyphenylamino)ethyl]-3-methyl-3H-imidazol-1-ium Monochloride Dihydrochloride

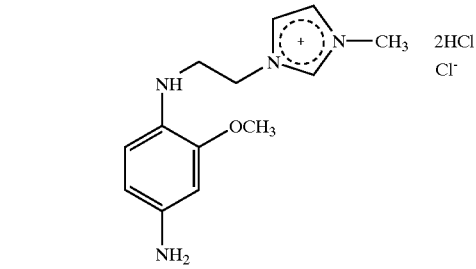

a) Preparation of 1-[2-(2-Methoxy-4-nitrophenylamino) ethyl]-3-methyl-3H-imidazol-1-ium Bromide A mixture of 46.8 g (0.17 mol) of (2-bromoethyl)-(2-methoxy-4-nitrophenyl)amine and 20.5 g (0.25 mol) of 1-methyl-1H-imidazole in 170 ml of toluene was refluxed for 7 hours.

The crystalline precipitate was filtered off, reimpasted in absolute ethanol and dried under vacuum at 50° . C.

50.2 g of yellow crystals melting at 184° C. (Kofler) were obtained, the elemental analysis of which, calculated for $C_{13}H_{17}N_4O_3Br$, was:

| % | C | H | N | O | Br |
|---|---|---|---|---|---|
| Calculated | 43.71 | 4.80 | 15.68 | 13.44 | 22.37 |
| Found | 43.59 | 4.85 | 15.66 | 14.25 | 22.03 | b) Reduction of 1-[2-(2-Methoxy-4-nitrophenylamino)ethyl]-3-methyl-3H-imidazol-1-ium Bromide The reduction is carried out according to the procedure described above for Example 1, step b).

Starting with 39.5 g (0.11 mol) of 1-[2-(2-methoxy-4-nitrophenylamino)ethyl]-3-methyl-3H-imidazol-1-ium bromide, and after heating in approximately 5N absolute hydrochloric ethanol in order to complete the anion exchange, 12.5 g of slightly grey crystals melting with decomposition at 210–218° C. (Kofler) were obtained, the elemental analysis of which, calculated for $C_{13}H_{21}N_4O_3 \cdot \frac{1}{2}H_2O$ was:

| % | C | H | N | O | Cl |
|---|---|---|---|---|---|
| Calculated | 42.81 | 6.08 | 15.36 | 6.58 | 29.16 |
| Found | 42.42 | 5.99 | 14.88 | 6.14 | 29.55 |

Preparation Example 9

Synthesis of 1-(5-Amino-2-hydroxybenzyl)-3-methyl-3H-imidazol-1-ium Monochloride Hydrochloride

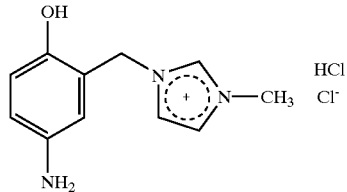

a) Preparation of 1-(2-Hydroxy-5-nitrobenzyl)-3-methyl-3H-imidazol-1-ium Chloride The procedure described for Example 8, step a) is used.

Starting with 56.3 g (0.3 mol) of 2-chloromethyl-4-nitrophenol and 29.6 g (0.36 mol) of 1-methyl-1H-imidazole, 65.1 g of yellow crystals melting with decomposition at 250–260° C. (Kofler) were obtained, the elemental analysis of which, calculated for $C_{11}H_{12}N_3O_3Cl$, was:

| % | C | H | N | O | Cl |
|---|---|---|---|---|---|
| Calculated | 48.99 | 4.49 | 15.58 | 17.80 | 13.15 |
| Found | 48.74 | 4.58 | 15.72 | 17.62 | 13.27 | b) Reduction of 1-(2-Hydroxy-5-nitrobenzyl)-3-methyl-3H-imidazol-1-ium Chloride 27.5 g, (0.102 mol) of 1-(2-hydroxy-5-nitrobenzyl)-3-methyl-3H-imidazol-1-ium chloride obtained in the previous step, 10 g of 5% palladium on charcoal (containing 50% water) and 400 ml of water were placed in a hydrogenator.

The reduction took place over one hour at a hydrogen pressure of about 4 bar and at a temperature which was gradually raised to 35° C.

After filtering off the catalyst under nitrogen, aqueous hydrochloric acid was run in.

The filtrate was evaporated to dryness under reduced pressure and the crude product was taken up in absolute ethanol and filtered off.

After drying at 40° C. under vacuum and over potassium hydroxide, 23.5 g of white crystals melting at 170–175° C. (Kofler) were obtained, the elemental analysis of which was in agreement with that calculated for $C_{11}H_{15}N_3OCl_2$.

The structure was in accordance by $^1H$ NMR.

Preparation Example 10

Synthesis of 3-[2-(2,5-Diaminophenyl)ethyl]-1-methyl-3H-imidazol-1-ium Chloride Dihydrochloride

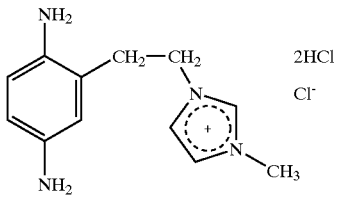

a) Preparation of N-[4-Acetylamino-2-(2-chloroethyl)phenyl]acetamide 135.0 g (0.6 mol) of 2-(2,5-diaminophenyl)ethanol dihydrochloride were dissolved in 700 ml of water at room temperature and a solution of 83.2 g (0.66 mol) of sodium sulphite in 166 ml of water was added.

140.8 ml (1.5 mol) of acetic anhydride were run in rapidly (exothermic reaction) and the suspension was stirred for two hours.

The crude product was filtered off, washed with water and dried under vacuum at 45° C. over phosphorus pentoxide.

115.1 g of white crystals of N-[4-acetyl-amino-2-(2-hydroxyethyl)phenyl]acetamide melting at 2020–were obtained.

64.1 g (0.272 mol) of this compound were dissolved in 500 ml of dimethylformamide and 53.0 ml (0.38 mol) of triethylamine at room temperature.

25.3 ml (0.326 mol) of mesyl chloride were cooled to about 0° C. and run in dropwise with stirring, while keeping the temperature between 0 and 5° C.

The triethylamine hydrochloride formed was filtered off and 90.0 g (2.12 mol) of lithium chloride were added to the filtrate. This mixture was heated for 15 minutes with stirring at a temperature of 110–115° C.

The mixture was poured into 1 kg of ice-cold water and the crystalline precipitate was filtered off, washed with water and recrystallized from refluxing isopropanol.

53.4 g of white crystals of N-[4-acetylamino-2-(2-chloroethyl)phenyl]acetamide melting at 214–216° C. were obtained, the elemental analysis of which, calculated for $C_{12}H_{15}N_2O_2C$ was:

| % | C | H | N | O | Cl |
|---|---|---|---|---|---|
| Calculated | 56.59 | 5.94 | 11.00 | 12.56 | 13.92 |
| Found | 56.31 | 6.05 | 11.10 | 12.95 | 13.92 | b) Quaternization and Deacetylation

A mixture of 25.5 g (0.1 mol) of N-[4-acetyl-amino-2-(2-chloroethyl)phenyl]acetamide obtained above in the previous step and 17.5 ml (0.22mol) of 1-methyl-1H-imidazole in 150 ml of toluene and 210 ml of isobutanol was refluxed for 18 hours.

The mixture was evaporated to dryness under reduced pressure.

The 3-[2-(2,5-bis(acetylamino)phenyl)ethyl]-1-methyl-3H-imidazol-1-ium gum obtained was then refluxed for 6 hours in 100 ml of aqueous 36% hydrochloric acid.

The mixture was evaporated to dryness under reduced pressure and the crystalline precipitate was taken up in isopropanol and filtered off.

After drying at 40° C. under vacuum and over phosphorus pentoxide, 24.7 g of cream-coloured crystals of 3-[2-(2,5-diaminophenyl)ethyl]-1-methyl-3H-imidazol-1-ium chloride dihydrochloride melting with decomposition at over 260° C. (Kofler) were obtained, the elemental analysis of which, calculated for $C_{12}H_{19}N_4Cl_3 \cdot \frac{1}{2}H_2O$, was:

| % | C | H | N | O | Cl |
|---|---|---|---|---|---|
| Calculated | 43.07 | 6.02 | 16.74 | 2.39 | 31.78 |
| Found | 43.29 | 6.25 | 16.62 | 2.21 | 32.06 |

Preparation Example 11

Synthesis of 1-{2-[(4-Aminophenyl)ethylaminol]ethyl}-3-methyl-3H-imidazol-1-ium Chloride Dihydrochloride

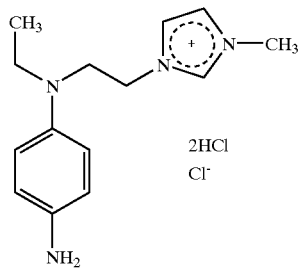

a) Preparation of N-{4-[(2Chloroethyl)ethylamino]phenyl}acetamide 66.7 g (0.3 mol) of N-{4-[ethyl-(2-hydroxyethyl)amino]phenyl}acetamide were dissolved in 500 ml of dimethylformamide and 58.5 ml (0.42 mol) of triethylamine at room temperature.

28.0 ml (0.36 mol) of mesyl chloride were cooled to about 0° C. and run in dropwise with stirring, while keeping the temperature between 0 and 5° C.

The triethylamine hydrochloride formed was filtered off and 38.2 g (0.9 mol) of lithium chloride were added to the filtrate.

The mixture was heated with stirring for 15 minutes at 100–108° C.

The mixture was poured into 1 kg of ice-cold water and the crystalline precipitate was filtered off, washed with water and recrystallized from refluxing isopropanol.

62.7 g of white crystals of N-{4-[(2-chloroethyl)ethylamino]phenyl}acetamide melting at 102° C. were obtained, the elemental analysis of which, calculated for $C_{12}H_{17}N_2OCl$, was:

| % | C | H | N | O | Cl |
|---|---|---|---|---|---|
| Calculated | 59.87 | 7.12 | 11.64 | 6.65 | 14.73 |
| Found | 59.42 | 7.10 | 11.33 | 7.54 | 14.42 | b) Quaternization of N-{4-[(2Chloroethyl)ethylamino]phenyl}acetamide

A mixture of 24.1 g (0.1 mol) of N-{4-[(2-chloroethyl)ethylamino]phenyl}acetamide obtained above in the previous step and 17.5 ml (0.22 mol) of 1-methyl-1H-imidazole in 70 ml of isobutanol was refluxed for 4hours.

The mixture was cooled to about 0° C. and 140 ml of toluene were added.

The crystalline precipitate was filtered off, washed with toluene and then with petroleum ether, and dried under vacuum at 45° C. over phosphorus pentoxide.

31.5 g of white crystals of 3-{2-[(4-acetyl-aminophenyl)ethylamino]ethyl}-1-methyl-3H-imidazol-1-ium chloride melting at 206° C. were obtained, the elemental analysis of which, calculated for $C_{16}H_{23}N_4OCl \cdot \frac{1}{4}H_2O$, was:

| % | C | H | N | O | Cl |
|---|---|---|---|---|---|
| Calculated | 58.71 | 7.24 | 17.12 | 6.11 | 10.83 |
| Found | 58.77 | 7.18 | 17.25 | 6.05 | 10.68 | c) Deacetylation of 3-{2-[(4-Acetylaminophenyl)ethylamino]ethyl}-1-methyl-3H-imidazol-1-ium Chloride 29 g (0.09 mol) of 3-{2-[(4-acetylamino-phenyl)ethylamino]ethyl}-1-methyl-3H-imidazol-1-ium chloride obtained above in the previous step were refluxed for 1 hour in 30 ml of 36% hydrochloric acid. The mixture was evaporated to dryness under reduced pressure and the crystalline precipitate was taken up in absolute ethanol, precipitated by dilution with ethyl ether, filtered off and dried. 13.4 g of white crystals of 1-{2-[(4-aminophenyl)ethylamino]ethyl}-3-methyl-3H-imidazol-1-ium chloride dihydrochloride melting with decomposition at 212–214° C. (Kofler) were obtained, the $^1$H NMR of which was in agreement with that of the expected product.

Preparation Example 12

Synthesis of N,N-bis[2-(3-Methyl-3H-imidazol-1-ium)ethyl]-4-aminoaniline Dichloride Monohydrochloride Monohydrate

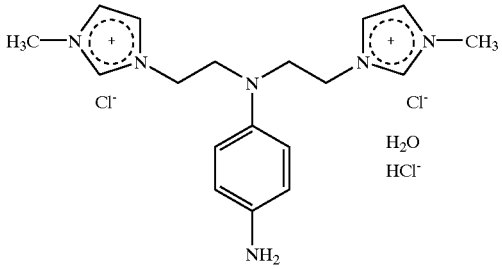

a) Preparation of N,N-bis[2-(3-Methyl-3H-imidazol-1-ium)ethyl]-4-nitroaniline Dichloride Dihydrate A mixture of 31.5 g (0.12 mol) of bis(2-chloroethyl)(4-nitrophenyl)amine and 59.1 g (0.72 mol) of 1-methyl-1H-imidazole in 60 ml of toluene was refluxed for 6 hours.

The crystalline precipitate formed was filtered off while hot, washed with toluene and recrystallized from a refluxing mixture of water and ethanol.

45.0 g of yellow crystals of N,N-bis[2-(3-methyl-3H-imidazol-1-ium)ethyl]-4-nitroaniline dichloride dihydrate melting with decomposition at above 260° C. were obtained, the elemental analysis of which, calculated for $C_{18}H_{24}N_6Cl_2 \cdot 2H_2O$, was:

| % | C | H | N | O | Cl |
|---|---|---|---|---|---|
| Calculated | 46.66 | 6.09 | 18.14 | 13.81 | 15.30 |
| Found | 46.72 | 6.20 | 18.12 | 13.85 | 15.25 | b) Reduction of N,N-bis[2-(3-Methyl-3H-imidazol-1-ium)ethyl]-4-nitroaniline Dichloride Dihydrate 45.0 g (0.105 mol) of N,N-bis[2-(3-methyl-3H-imidazol-1-ium)ethyl]-4-nitroaniline dichloride dihydrate obtained above in the previous step, 16 g of 5% palladium on charcoal (containing 50% water), 300 ml of ethanol and 300 ml of water were placed in a hydrogenator.

The reduction took place over one hour at a hydrogen pressure of about 8 bar and at a temperature which was gradually raised to 80° C.

After filtering off the catalyst under nitrogen, the mixture was poured onto 36% hydrochloric acid.

The mixture was evaporated to dryness under reduced pressure and the crude product was taken up in absolute ethanol and filtered off.

After recrystallization from refluxing 96 ° ethanol, 28.2 g of white crystals of N,N-bis[2-(3-methyl-3H-imidazol-1-ium)ethyl]-4-aminoaniline dichloride monohydrochloride monohydrate melting with decomposition at above 260° C. (Kofler) were obtained, the elemental analysis of which, calculated for $C_{18}H_{27}N_6Cl_3 \cdot H_2O$, was:

| % | C | H | N | O | Cl |
|---|---|---|---|---|---|
| Calculated | 47.85 | 6.47 | 18.60 | 3.54 | 2.54 |
| Found | 46.93 | 6.55 | 18.03 | | 23.72 |

Preparation Example 13

Synthesis of 3-[2-(4-Aminophenylamino)butyl]-1-methyl-3H-imidazol-1-ium Chloride Dihydrochloride

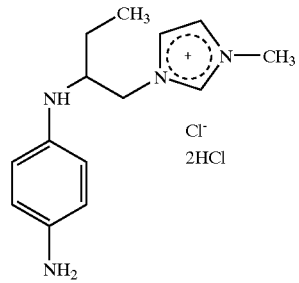

a) Preparation of 2-(4-Nitrophenylamino)butan-1-ol

A mixture of 223.0 g (1.58 mol) of 1-fluoro-4-nitrobenzene, 168.5 g (1.89 mol) of 2-amino-1-butanol and 146.8 g (1.06 mol) of potassium carbonate in 630 ml of water was refluxed for 2 hours.

The mixture was cooled to room temperature, the aqueous phase was removed and the orange-coloured oil was taken up in ethyl acetate.

After washing the ethyl acetate phase with water, drying over anhydrous sodium sulphate, filtration, evaporation to dryness under reduced pressure and recrystallization from refluxing 96° C. ethanol, 84.4 g of orange-coloured crystals of 2-(4-nitrophenylamino)butan-1-ol melting at 90° C. (Kofler) were obtained, the elemental analysis of which, calculated for $C_{10}H_{14}N_2O_3$, was:

| % | C | H | N | O |
|---|---|---|---|---|
| Calculated | 57.13 | 6.71 | 13.32 | 22.83 |
| Found | 57.17 | 6.73 | 13.36 | 22.75 | b) Preparation of (1-Chloromethylpropyl)-(4-nitro-phenyl)amine

The procedure described above in Example 11, step a) was used.

Starting with 63.1 g (0.3 mol) of 2-(4-nitro-phenylamino)butan-1-ol obtained above in the previous step, and after recrystallization from refluxing 900 ethanol, 47.8 g of yellow crystals of (1-chloromethyl-propyl)-(4-nitrophenyl)amine melting at 50–52° C. were obtained, the elemental analysis of which, calculated for $C_{10}H_{13}N_2O_2Cl$, was:

| % | C | H | N | O | Cl |
|---|---|---|---|---|---|
| Calculated | 52.52 | 5.73 | 12.25 | 13.99 | 15.50 |
| Found | 52.46 | 5.89 | 12.14 | 13.91 | 15.55 | c) Preparation of 1-Methyl-3-[2-(4-nitrophenylamino)butyl]-3H-imidazol-1-ium Chloride A mixture of 22.9 g (0.1 mol) of (1-chloromethylpropyl)-(4-nitrophenyl)amine obtained above in the previous step and 17.5 ml (0.22 mol) of 1-methyl-1H-imidazole in 70 ml of toluene was refluxed for 9 hours.

The crystalline precipitate was filtered off, washed with toluene and then with petroleum ether, and recrystallized from refluxing isopropanol.

16.0 g of yellow crystals of 1-methyl-3-[2-(4-nitrophenylamino)butyl]-3H-imidazol-1-ium chloride melting at 191° C. were obtained, the elemental analysis of which, calculated for $C_{14}H_{19}N_4O_2Cl \cdot \frac{1}{2}H_2O$, was:

| % | C | H | N | O | Cl |
|---|---|---|---|---|---|
| Calculated | 52.58 | 6.30 | 17.52 | 12.51 | 11.09 |
| Found | 52.03 | 6.23 | 17.01 | 12.76 | 10.94 | d) Reduction of 1-Methyl-3-[2-(4-nitrophenylamino)butyl]-3H-imidazol-1-ium Chloride The procedure described above in Example 12, step b) was used.

After recrystallization from a refluxing mixture of 96° C. ethanol and 36° C. hydrochloric acid, 18.6 g of white crystals of 1-methyl-3-[2-(4-nitrophenylamino)butyl]-3H-imidazol-1-ium chloride dihydrochloride melting at 214–2160° C. were obtained, the elemental analysis of which, calculated for $C_{14}H_{23}N_4Cl_3$, was:

| % | C | H | N | Cl |
|---|---|---|---|---|
| Calculated | 47.54 | 6.55 | 15.84 | 30.07 |
| Found | 47.02 | 6.69 | 15.71 | 29.50 |

Preparation Example 14

Synthesis of 1-{[5-Amino-2-(2-hydroxyethylamino)phenylcarbamoyl]methyl}-3-methyl-3H-imidazol-1-ium Chloride Dihydrochloride

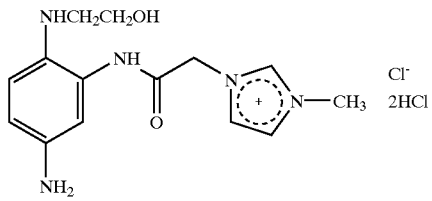

a) Preparation of 2-Chloro-N-[2-(2-hydroxyethylamino)-5-nitrophenyl]acetamide

A mixture of 82.5 g (0.418 mol) of 2-(2-amino-4-nitrophenylamino)ethanol and 34.6 g (0.25 mol) of potassium carbonate in 400 ml of dimethylformamide was cooled to 5° C.

34.7 ml of chloroacetyl chloride were added dropwise, while keeping the temperature between 5 and 12° C.

The mixture was stirred for a further one hour.

The resulting mixture was poured onto a mixture of 2 liters of ice-cold water and 100 ml of 36% hydrochloric acid.

The crystalline precipitate was filtered off, washed with water, dried and recrystallized from refluxing acetonitrile.

74.2 g of yellow crystals of 2-chloro-N-[2-(2-hydroxyethylamino)-5-nitrophenyl]acetamide melting at 206° C. were obtained, the elemental analysis of which, calculated for $C_{10}H_{12}N_3O_4Cl$, was:

| % | C | H | N | O | Cl |
|---|---|---|---|---|---|
| Calculated | 43.89 | 4.42 | 15.35 | 23.38 | 12.95 |
| Found | 43.83 | 4.63 | 15.23 | 22.87 | 13.00 | b) Preparation of 1-{[2-(2-Hydroxyethylamino)-5-nitrophenylcarbamoyl]methyl}-3-methyl-3H-imidazol-1-ium Chloride A suspension of 42.0 g (0.15 mol) of 2-chloro-N-[2-(2-hydroxyethylamino)-5-nitrophenyl]-acetamide obtained above in the previous step and 24.6 g (0.3 mol) of 1-methyl-1H-imidazole in 150 ml of toluene was refluxed for one hour.

30 ml of isobutanol were added and refluxing was continued for 2 hours.

The mixture was cooled to room temperature and the crude product was filtered off, washed with toluene and recrystallized from a refluxing mixture of ethanol and water. 37.9 g of yellow crystals of 1-{[2-(2-hydroxyethylamino)-5-nitrophenylcarbamoyl]methyl}-3-methyl-3H-imidazol-1-ium chloride melting at 200° C. were obtained, the elemental analysis of which, calculated for $C_{14}H_{18}N_5O_4Cl$, was:

| % | C | H | N | O | Cl |
|---|---|---|---|---|---|
| Calculated | 47.26 | 5.10 | 19.68 | 17.99 | 9.96 |
| Found | 48.04 | 5.20 | 19.87 | 17.03 | 10.28 | c) Reduction of 1-{[2-(2-Hydroxyethylamino)-5-nitrophenylcarbamoyl]methyl}-3-methyl-3H-imidazol-1-ium Chloride The procedure described above in Example 12, step b) was used.

Starting with 37.9 g of 1-{[2-(2-hydroxy-ethylamino)-5-nitrophenylcarbamoyl]methyl}-3-methyl-3H-imidazol-1-ium chloride obtained in the previous step, 37.1 g of white crystals of 1-{[5-amino-2-(2-hydroxy-ethylamino)phenylcarbamoyl]methyl-}3-methyl-3H-imidazol-1-ium chloride dihydrochloride melting with decomposition at about 240° C. were obtained, the $^1$H NMR of which was in accordance with that of the expected product.

APPLICATION EXAMPLES

Examples 1 to 13 of Dyeing in Basic Medium

The following dye compositions were prepared (contents in grams):

| EXAMPLE | 1 | 2 | 3 | 4 | 5 | 6 | 7 | 8 | 9 | 10 | 11 | 12 | 13 |
|---|---|---|---|---|---|---|---|---|---|---|---|---|---|
| 3-[3-(4-Aminophenylamino)-propyl]-1-methyl-3H-imidazol-1-ium monochloride dihydrochloride (compound of formula (I)) | 1.036 | 1.036 | — | — | — | — | — | — | — | — | — | — | — |
| 1-[3-(2,5-Diaminophenoxy)-propyl]-3-methyl-3H-imidazol-1-ium monochloride dihydrochloride (compound of formula (I)) | — | — | 1.066 | 1.066 | — | — | — | — | — | — | — | — | — |
| 3-[3-(4-Amino-3-methylphenyl-amino)propyl]-1-methyl-3H-imidazol-1-ium monochloride dihydrochloride (compound of formula (I)) | — | — | — | — | 1.061 | 1.061 | 1.061 | 1.061 | — | — | — | — | — |
| 3-[3-(4-Amino-2-methyl-phenylamino)propyl]-1-methyl-3H-imidazol-1-ium monochloride dihydrochloride (compound of formula (I)) | — | — | — | — | — | — | — | — | 1.087 | 1.087 | — | — | — |

-continued

| EXAMPLE | 1 | 2 | 3 | 4 | 5 | 6 | 7 | 8 | 9 | 10 | 11 | 12 | 13 |
|---|---|---|---|---|---|---|---|---|---|---|---|---|---|
| 1-[2-(4-Amino-2-methoxy-phenylamino)ethyl]-3-methyl-3H-imidazol-1-ium monochloride dihydrochloride (compound of formula (I)) | — | — | — | — | — | — | — | — | — | — | 1.094 | — | — |
| 3-[3-(4-Amino-2-fluoro-phenylamino)propyl]-1-methyl-3H-imidazol-1-ium monochloride dihydrochloride (compound of formula (I)) | — | — | — | — | — | — | — | — | — | — | — | 1.126 | — |
| 3-[3-(4-Amino-2-cyanophenyl-amino)propyl]-1-methyl-3H-imidazol-1-ium monochloride dihydrochloride (compound of formula (I)) | — | — | — | — | — | — | — | — | — | — | — | — | 0.985 |
| Resorcinol (coupler) | — | — | — | 0.33 | — | 0.33 | — | — | — | 0.33 | — | — | — |
| meta-Aminophenol (coupler) | — | — | — | — | — | — | 0.327 | — | — | — | — | — | — |
| 2-Methyl-5-N-(β-hydroxy-ethyl)aminophenol (coupler) | 0.543 | — | — | — | — | — | — | — | — | — | — | — | — |
| 2,4-Diaminophenoxyethanol dihydrochloride (coupler) | — | 0.675 | — | — | — | — | — | 0.675 | — | — | 0.675 | — | — |
| Common dye support | (*) | (*) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g | 100 g | 100 g |

| (*) Common dye support: | |
|---|---|
| 96° Ethanol | 20 g |
| Pentasodium salt of diethylenetriamine-pentaacetic acid sold under the name Masquol DTPA by the company Protex | 1.08 g |
| Sodium metabisulphite as an aqueous solution containing 35% A.M. | 0.58 g A.M. |
| 20% Aqueous ammonia | 10 g |

At the time of use, each of the above dye compositions was mixed, weight for weight, with a 20-volumes hydrogen peroxide solution (6% by weight) of pH 3.

The mixture obtained was applied to locks of natural or permanent-waved grey hair containing 90% white hairs, for 30 minutes. The locks were then rinsed, washed with a standard shampoo, rinsed again and then dried.

The shades obtained are given in the table below:

| EXAMPLE | DYEING pH | Shade on natural hair | Shade on permanent-waved hair |
|---|---|---|---|
| 1 | 10 + 0.2 | Ash-purple | Deep purple |
| 2 | 10 + 0.2 | Deep blue | Deep blue |
| 3 | 10 + 0.2 | Golden beige | Golden ash |
| 4 | 10 + 0.2 | Iridescent golden ash | Natural violet |
| 5 | 10 + 0.2 | Matt golden | Matt golden |
| 6 | 10 + 0.2 | Matt golden ash | Matt golden ash |
| 7 | 10 + 0.2 | Ash-grey | Ash-grey |
| 8 | 10 + 0.2 | Green-blue | Green-blue |
| 9 | 10 + 0.2 | Slightly iridescent mahogany | Slightly iridescent mahogany |
| 10 | 10 + 0.2 | Mahogany-ash | Violet-ash |
| 11 | 10 + 0.2 | Ash-grey | Ash-grey |
| 12 | 10 + 0.2 | Iridescent purple | Iridescent purple |
| 13 | 10 + 0.2 | Iridescent mahogany | Iridescent mahogany |

Examples 14–17 of Dyeing in Basic Medium

The following dye compositions were prepared (contents in grams):

| EXAMPLE | 14 | 15 | 16 | 17 |
|---|---|---|---|---|
| 3-[2-(2,5-Diaminophenyl)ethyl]-1-methyl-3H-imidazol-1-ium chloride dihydrochloride (compound of formula (I)) | 0.98 | — | — | — |
| 1-{2-[(4-Aminophenyl)ethylamino]-ethyl}-3-methyl-3H-imidazol-1-ium chloride dihydrochloride (compound of formula (I)) | — | 1.06 | — | — |
| N,N-bis[2-(3-Methyl-3H-imidazol-1-ium)ethyl]-4-aminoaniline dichloride monohydrochloride monohydrate (compound of formula (I)) | — | — | 1.41 | — |
| 3-[2-(4-Aminophenylamino)butyl]-1-methyl-3H-imidazol-1-ium chloride dihydrochloride (compound of formula (I)) | — | — | — | 1.06 |
| 2,4-Diamino-1-(β-hydroxyethyloxy)-benzene dihydrochloride (coupler) | 0.723 | — | — | — |
| 3-Aminophenol (coupler) | — | 0.327 | — | — |
| 6-Hydroxyindole (coupler) | — | — | 0.399 | — |
| 5-N-(β-Hydroxyethyl)amino-2-methyl-phenol (coupler) | — | — | — | 0.498 |
| Common dye support | (*) | (*) | (*) | (*) |
| Demineralized water qs | 100 g | 100 g | 100 g | 100 g |

(*) Common Dye Support:

This is identical to the one used for the above Dyeing Examples 1 to 13.

At the time of use, each of the above dye compositions was mixed, weight for weight, with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 14 | 10 + 0.2 | Violet-blue |
| 15 | 10 + 0.2 | Violet-ash chestnut |
| 16 | 10 + 0.2 | Coppery-golden light chestnut |
| 17 | 10 + 0.2 | Purple |

What is claimed is:

1. A compound of formula (I) or an acid addition salt thereof:

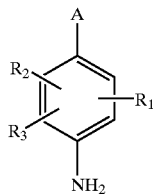

(1)

wherein:
R$_1$, R$_2$ and R$_3$, are identical or different and represent
- a hydrogen atom;
- a halogen atom;
- a group Z;
- a (C$_1$–C$_6$)alkylcarbonyl radical;
- an amino(C$_1$–C$_6$)alkylcarbonyl radical;
- an N—Z-amino(C$_1$–C$_6$)alkylcarbonyl radical;
- an N—(C$_1$–C$_6$)alkylamino(C$_1$–C$_6$)alkylcarbonyl radical;
- an N,N-di(C$_1$–C$_6$)alkylamino(C$_1$–C$_6$)alkylcarbonyl radical;
- an amino(C$_1$–C$_6$)alkylcarbonyl(C$_1$–C$_6$)alkyl radical;
- an N—Z-amino(C$_1$–C$_6$)alkylcarbonyl(C$_1$–C$_6$)alkyl radical;
- an N—(C$_1$–C$_6$)alkylamino(C$_1$–C$_6$)alkylcarbonyl(C$_1$–C$_6$)alkyl radical;
- an N,N—di(C$_1$–C$_6$)alkylamino(C$_1$–C$_6$)alkylcarbonyl(C$_1$–C$_6$)alkyl radical;
- a carboxyl radical;
- a (C$_1$–C$_6$)alkylcarboxyl radical;
- a C$_1$–C$_6$ alkylsulphonyl radical;
- an aminosulphonyl radical;
- an N—Z-aminosulphonyl radical;
- a C$_1$–C$_6$ N-alkylaminosulphonyl radical;
- an N,N-di(C$_1$–C$_6$)alkylaminosulphonyl radical;
- an aminosulphonyl(C$_1$–C$_6$)alkyl radical;
- an N—Z-aminosulphonyl(C$_1$–C$_6$)alkyl radical;
- an N—(C$_1$–C$_6$)alkylaminosulphonyl(C$_1$–C$_6$)alkyl radical;
- an N,N-di(C$_1$–C$_6$)alkylaminosulphonyl(C$_1$–C$_6$)alkyl radical;
- a carbamyl radical;
- an N—(C$_1$–C$_6$)alkylcarbamyl radical;
- an N,N-di(C$_1$–C$_6$)alkylcarbamyl radical;
- a carbamyl(C$_1$–C$_6$)alkyl radical;
- an N—(C$_1$–C$_6$)alkylcarbamyl(C$_1$–C$_6$)alkyl radical;
- an N,N-di(C$_1$–C$_6$)alkylcarbamyl(C$_1$–C$_6$)alkyl radical;
- a C$_1$–C$_6$ alkyl radical;
- a monohydroxy(C$_1$–C$_6$)alkyl radical;
- a polyhydroxy(C$_2$–C$_6$)alkyl radical;
- a (C$_1$–C$_6$)alkoxy(C$_1$–C$_6$)alkyl radical;
- a trifluoro(C$_1$–C$_6$)alkyl radical;
- a cyano radical;
- a group OR$_6$;
- a group SR$_6$;
- an amino group protected with a (C$_1$–C$_6$)alkylcarbonyl, (C$_1$–C$_6$)alkylcarboxyl, trifluoro(C$_1$–C$_6$)alkylcarbonyl, amino(C$_1$–C$_6$)alkylcarbonyl, N—Z-amino(C$_1$–C$_6$)alkylcarbonyl, N—(C$_1$–C$_6$)alkylamino(C$_1$–C$_6$)alkylcarbonyl, N,N-di(C$_1$–C$_6$)alkylamino(C$_1$–C$_6$)alkylcarbonyl, carbamyl, N—(C$_1$–C$_6$)alkylcarbamyl, N,N-di(C$_1$–C$_6$)alkylcarbamyl, C$_1$–C$_6$ alkylsulphonyl, aminosulphonyl, N—Z-amino-sulphonyl, C$_1$–C$_6$ N—alkylaminosulphonyl, N,N-di(C$_1$–C$_6$)alkylaminosulphonyl, thiocarbamyl or formyl radical, or with a group Z;
- an amino(C$_1$–C$_6$)alkyl radical wherein the amine is substituted with one or two identical or different radicals selected from C$_1$–C$_6$ alkyl, monohydroxy(C$_1$–C$_6$)alkyl, polyhydroxy(C$_2$–C$_6$)alkyl, C$_1$–C$_6$ alkylcarbonyl, carbamyl, N—(C$_1$–C$_6$)alkylcarbamyl, N,N-di(C$_1$–C$_6$)alkylcarbamyl, (C$_1$–C$_6$)alkylsulphonyl, formyl, trifluoro(C$_1$–C$_6$)alkylcarbonyl, (C$_1$–C$_6$)alkylcarboxyl and thiocarbamyl radicals, or with a group Z;

R$_6$ denotes
- a C$_1$–C$_6$ alkyl radical;
- a monohydroxy(C$_1$–C$_6$)alkyl radical;
- a polyhydroxy(C$_2$–C$_6$)alkyl radical;
- a group Z;
- a (C$_1$–C$_6$)alkoxy(C$_1$–C$_6$)alkyl radical;
- an ary radical
- benzyl radical;
- a carboxy(C$_1$–C$_6$)alkyl radical;
- a (C$_1$–C$_6$)alkylcarboxy(C$_1$–C$_6$)alkyl radical;
- a cyano(C$_1$–C$_6$)alkyl radical;
- a carbamyl(C$_1$–C$_6$)alkyl radical;
- an N—(C$_1$–C$_6$)alkylcarbamyl(C$_1$–C$_6$)alkyl radical;
- an N,N-di(C$_1$–C$_6$)alkylcarbamyl(C$_1$–C$_6$)alkyl radical;
- a trifluoro(C$_1$–C$_6$)alkyl radical;
- an aminosulphonyl(C$_1$–C$_6$)alkyl radical;
- an N—Z-aminosulphonyl(C$_1$–C$_6$)alkyl radical;
- an N—(C$_1$–C$_6$)alkylaminosulphonyl(C$_1$–C$_6$)alkyl radical;
- an N,N-di(C$_1$–C$_6$)alkylaminosulphonyl(C$_1$–C$_6$)alkyl radical;
- a (C$_1$–C$_6$)alkylsulphinyl(C$_1$–C$_6$)alkyl radical;
- a (C$_1$–C$_6$)alkylsulphonyl(C$_1$–C$_6$)alkyl radical;
- a (C$_1$–C$_6$)alkylcarbonyl(C$_1$–C$_6$)alkyl radical;
- an amino(C$_1$–C$_6$)alkyl radical;
- an amino(C$_1$–C$_6$)alkyl radical wherein the amine is substituted with one or two identical or different radicals selected from C$_1$–C$_6$ alkyl, monohydroxy(C$_1$–C$_6$)alkyl, polyhydroxy(C$_2$–C$_6$)alkyl, (C$_1$–C$_6$)alkylcarbonyl, formyl, trifluoro(C$_1$–C$_6$)alkylcarbonyl, (C$_1$–C$_6$)alkylcarboxyl, carbamyl, N—(C$_1$–C$_6$)alkylcarbamyl, N,N-di(C$_1$–C$_6$)alkylcarbamyl, thiocarbamyl and C$_1$–C$_6$ alkylsulphonyl radicals, and the group Z;

A represents a group —NR$_4$R$_5$ or a hydroxyl radical;
R$_4$ and R$_5$, are identical or different and represent
- a hydrogen atom;
- a group Z;
- a C$_1$–C$_6$ alkyl radical;
- a monohydroxy(C$_1$–C$_6$)alkyl radical;
- a polyhydroxy(C$_2$–C$_6$)alkyl radical;
- a (C$_1$–C$_6$)alkoxy(C$_1$–C$_6$)alkyl radical;
- an aryl radical;
- a benzyl radical;
- a cyano(C$_1$–C$_6$)alkyl radical;
- a carbamyl(C$_1$–C$_6$)alkyl radical;
- an N—(C$_1$–C$_6$)alkylcarbamyl(C$_1$–C$_6$)alkyl radical;
- an N,N-di(C$_1$–C$_6$)alkylcarbamyl(C$_1$–C$_6$)alkyl radical;
- a thiocarbamyl(C$_1$–C$_6$)alkyl radical;
- a trifluoro(C$_1$–C$_6$)alkyl radical;
- a
- a sulpho(C$_1$–C$_6$)alkyl radical;
- a (C$_1$–C$_6$)alkylcarboxy(C$_1$–C$_6$)alkyl radical;
- a (C$_1$–C$_6$)alkylsulphinyl(C$_1$–C$_6$)alkyl radical;

an aminosulphonyl($C_1$–$C_6$)alkyl radical;
an N—Z-aminosulphonyl($C_1$–$C_6$)alkyl radical;
an N—($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_2$–$C_6$)alkyl, ($C_1$–$C_6$)alkylcarbonyl, carbamyl, N—($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z is selected from the unsaturated cationic groups of formulae (II) and (III), and the saturated cationic groups of formula (IV):

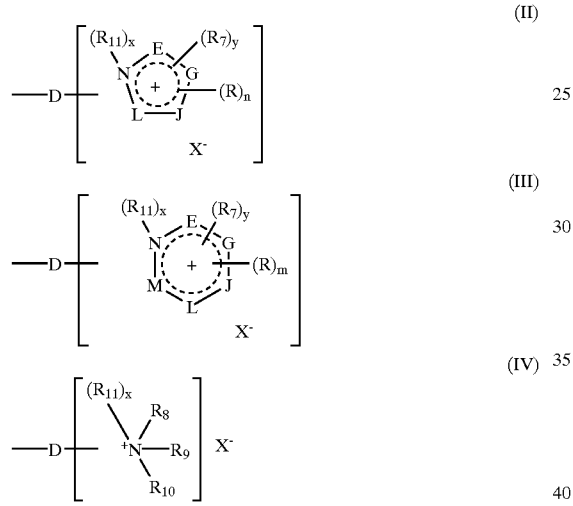

wherein:
D is a divalent linker arm which represents a linear or branched alkyl chain, said alkyl chain being uninterrupted or interrupted by at least one hetero atom, and said alkyl chain being unsubstituted or substituted with at least one hydroxyl or $C_1$–$C_6$ alkoxy radical, and said alkyl chain optionally having at least one ketone function;
the ring members E, G, J, L and M, are identical or different and represent a carbon, oxygen, sulphur or nitrogen atom;
n is an integer ranging from 0 and 4 inclusive;
m is an integer ranging from 0 and 5 inclusive;
the radicals R, are identical or different and represent group Z,
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a ($C_1$–$C_6$)alkylcarbonyl radical,
a thio radical,
a thio($C_1$–$C_6$)alkyl radical,
a $C_1$–$C_6$ alkylthio radical,
an amino radical,
an amino radical protected with a ($C_1$–$C_6$)alkylcarbonyl, carbamyl or $C_1$–$C_6$ alkylsulphonyl radical;
a group NHRO or NROR wherein RO and R, are identical or different and represent a $C_1$–$C_6$ alkyl radical, a monohydroxy($C_1$–$C_6$)alkyl radical or a polyhydroxy($C_2$–$C_6$)alkyl radical;

$R_7$ represents
a $C_1$–$C_6$ alkyl radical,
a monohydroxy($C_1$–$C_6$)alkyl radical,
a polyhydroxy($C_2$–$C_6$)alkyl radical,
a cyano($C_1$–$C_6$)alkyl radical,
a tri($C_1$–$C_6$)alkylsilane($C_1$–$C_6$)alkyl radical,
a ($C_1$–$C_6$)alkoxy($C_1$–$C_6$)alkyl radical,
a carbamyl($C_1$–$C_6$)alkyl radical,
a ($C_1$–$C_6$)alkylcarboxy($C_1$–$C_6$)alkyl radical,
a benzyl radical or
a group Z of formula (II), (III) or (IV) as defined above;

$R_8$, $R_9$ and $R_{10}$, are identical or different and represent
a $C_1$–$C_6$ alkyl radical,
a monohydroxy($C_1$–$C_6$)alkyl radical,
a polyhydroxy($C_2$–$C_6$)alkyl radical,
a ($C_1$–$C_6$)alkoxy($C_1$–$C_6$)alkyl radical,
a cyano($C_1$–$C_6$)alkyl radical,
an aryl radical,
a benzyl radical,
an amido($C_1$–$C_6$)alkyl radical,
a tri($C_1$–$C_6$)alkylsilane($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
two of the radicals $R_8$, $R_9$ and $R_1$ can together form, with the nitrogen atom to which they are attached, a saturated 5- or 6-membered ring, wherein said ring may contain at least one additional hetero atom, and further wherein said ring is unsubstituted or substituted with:
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a keto($C_1$–$C_6$)alkyl radical,
a thio radical,
a thio($C_1$–$C_6$)alkyl radical,
a $C_1$–$C_6$ alkylthio radical,
an amino radical or
an amino radical protected with a ($C_1$–$C_6$)alkylcarbonyl, carbamyl or $C_1$–$C_6$ alkylsulphonyl radical;
one of the radicals $R_8$, $R_9$ and $R_{10}$ may represent a second group Z which is identical to or different from the first group Z;

$R_{11}$ represents
  a $C_1$–$C_6$ alkyl radical;
  a monohydroxy($C_1$–$C_6$)alkyl radical;
  a polyhydroxy($C_2$–$C_6$)alkyl radical;
  an aryl radical;
  a benzyl radical;
  an amino($C_1$–$C_6$)alkyl radical, p2 an amino($C_1$–$C_6$) alkyl radical wherein the amine is protected with a ($C_1$–$C_6$)alkylcarbonyl, carbamyl or $C_1$–$C_6$ alkylsulphonyl radical;
  a carboxy($C_1$–$C_6$)alkyl radical;
  a cyano($C_1$–$C_6$)alkyl radical;
  a carbamyl($C_1$–$C_6$)alkyl radical;
  a trifluoro($C_1$–$C_6$)alkyl radical;
  a tri($C_1$–$C_6$)alkylsilane($C_1$–$C_6$)alkyl radical;
  a sulphonamido($C_1$–$C_6$)alkyl radical;
  a ($C_1$–$C_6$)alkylcarboxy($C_1$–$C_6$)alkyl radical;
  a ($C_1$–$C_6$)alkylsulphinyl($C_1$–$C_6$)alkyl radical;
  a ($C_1$–$C_6$)alkylsulphonyl($C_1$–$C_6$)alkyl radical;
  a ($C_1$–$C_6$)alkylketo($C_1$–$C_6$)alkyl radical;
an N—($C_1$–$C_6$)alkylcarbamyl($C_1$–$C_6$)alkyl radical;
  an N—($C_1$–$C_6$)alkylsulphonamido($C_1$–$C_6$)alkyl radical;
x and y are integers equal to 0 or 1; with the proviso that:
  in the unsaturated cationic groups of formula (II):
  when x=0, the divalent linker arm D is attached to the nitrogen
  atom,
  when x=1, the divalent linker arm D is attached to one of the ring members E G J or L,
  y can take the value 1 only:
    1) when the ring members E, G, J and L simultaneously represent a carbon atom and when the radical $R_7$ is borne by the nitrogen atom of the unsaturated ring; or
    2) when at least one of the ring members E, G, J and L represents a nitrogen atom to which the radical $R_7$ is attached;
  in the unsaturated cationic groups of formula (III):
  when x=0, the linker arm D is attached to the nitrogen atom,
  when x=1, the linker arm D is attached to one of the ring members E, G, J, L or M,
  y can take the value 1 only when at least one of the ring members E, G, J, L and M represents a divalent atom and when the radical $R_7$ is borne by the nitrogen atom of the unsaturated ring;
  in the cationic groups of formula (IV):
  when x=0, then the linker arm is attached to the nitrogen atom bearing the radicals $R_8$ to $R_{10}$,
  when x=1, then two of the radicals $R_8$ to $R_1$ form, together with the nitrogen atom to which they are attached, a saturated 5- or 6-membered ring as defined above, and the linker arm D is borne by a carbon atom of said saturated ring;
$X^-$ represents a monovalent or divalent anion; further with the provisos that:
  the number of unsaturated cationic groups Z of formula (II) or (III) in said compound or acid addition salt thereof is at least equal to 1;
  when A represents a group —$NP_4R_5$, wherein $R_4$ or $R_5$ represents a group Z wherein the divalent linker arm D represents an alkyl chain containing a ketone function, then said ketone function is not directly attached to the nitrogen atom of the group —$NR_4R_5$;
  wherein 4-amino-3-methyl-N-ethyl-N-∃-(1-pyridinium)ethylaniline chloride is excluded;

when:
  A is a hydroxyl radical,
  two of $R_1$, $R_2$ and $R_3$ are hydrogen atoms and one of $R_1$, $R_2$ and $R_3$ is a
  wherein:
    Z is a compound of formula (III), wherein:
      D is $CH_2$,
      x is 0,
      y is 0,
      E, G, J, L and M are carbon atoms, and
      m is 1,
  then, R is not chosen from hydroxy radicals; amino radicals; a $CH_2OH$ radical; groups NR"R'", wherein R" and R'" are each a ($C_1$–$C_4$)alkyl radical; ($C_1$–$C_4$) alkyl radicals; and fused aromatic rings;
when:
  A is a hydroxyl radical,
  two of $R_1$, $R_2$ and $R_3$ are hydrogen atoms and one of $R_1$, $R_2$ and $R_3$ is a group Z,
  wherein:
    Z is a compound of formula (III), wherein:
      D is $CH_2$,
      x is 0,
      y is 0,
      E, G, J, L and M are carbon atoms, and
      m is 2,
then:
  neither R is chosen from hydroxy radicals; amino radicals; groups NR"R'" wherein R" and R'" are each a ($C_1$–$C_4$)alkyl radical; ($C_1$–$C_4$)alkyl radicals; and fused aromatic rings; and
when:
  two of $R_1$, $R_2$ and $R_3$ are hydrogen atoms and one of $R_1$, $R_2$ and $R_3$ is a trifluoromethyl radical,
  A is $NR_4R_5$, wherein:
    one of $R_4$ and $R_5$ is chosen from a hydrogen atom and $C_1$–$C_4$ alkyl radicals, and
    one of $R_4$ and $R_5$ is a group Z, wherein:
      Z is a compound of formula (II), wherein:
        D is chosen from $C_1$–$C_3$ alkyl chains, and
        one of x, y and n is 1, and two of x, y, and n are 0, and
        two of E, J, G and L are nitrogen atoms such that a 1,2,4-triazolium ring is formed,
    then, $R_{11}$, $R_7$ and R, if present, are not $C_1$–$C_4$ alkyl radicals and $R_{11}$ and $R_7$ are not phenyl ($C_1$–$C_2$) alkyl radicals.

2. A compound according to claim 1, wherein said divalent linker D represents a linear alkyl chain comprising from 1 to 14 carbon atoms or a branched alkyl chain comprising from 3 to 14 carbon atoms, said alkyl chain being uninterrupted or interrupted by at least one hetero atom selected from oxygen, sulfur and nitrogen atoms.

3. A compound according to claim 1, wherein said rings of the unsaturated groups Z of formula (II) are selected from quaternized pyrrole, imidazole, pyrazole, oxazole, thiazole and triazole rings.

4. A compound according to claim 1, wherein said rings of the unsaturated groups Z of formula (III) are selected from quaternized pyridine, pyrimidine, pyrazine, oxazine and triazine rings.

5. A compound according to claim 1, wherein two of said radicals $R_8$, $R_9$ and $R_{10}$ form a quaternized pyrrolidine, a piperidine, a piperazine or a morpholine ring.

6. A compound according to claim 1, wherein said $X^-$ is selected from a halogen atom, a hydroxide, a hydrogenosulphate and a $C_1$–$C_6$ alkyl sulphate.

7. A compound according to claim 1, wherein said compound is:

1-[2-(4-aminophenylamino)ethyl]-3-methyl-3H-imidazol-1-ium bromide;
1-[3-(2,5-diaminophenoxy)propyl]-3-methyl-3H-imidazol-1-ium chloride;
3-[3-(4-aminophenylamino)propyl]-1-methyl-3H-imidazol-1-ium chloride;
3-[3-(4-amino-3-methylphenylamino)propyl]-1-methyl-3H-imidazol-1-ium chloride;
3-[3-(4-amino-2-methylphenylamino)propyl]-1-methyl-3H-imidazol-1-ium chloride;
3-[3-(4-amino-2-fluorophenylamino)propyl]-1-methyl-3H-imidazol-1-ium chloride monohydrate;
3-[3-(4-amino-2-cyanophenylamino)propyl]-1-methyl-3H-imidazol-1-ium chloride;
1-1-[2-(4-amino-2-methoxyphenylamino)ethyl]-3-methyl-3H-imidazol-1-ium chloride;
1-(5-amino-2-hydroxybenzyl)-3-methyl-3H-imidazol-1-ium chloride;
1-(5-amino-2-hydroxybenzyl)-2-methyl-2H-pyrazol-1-ium chloride;
1-[2-(2,5-diaminophenyl)ethyl]-3-methyl-3H-imidazol-1-ium chloride;
3-[2-(2,5-diaminophenyl)ethyl]-1-methyl-3H-imidazol-1-ium chloride;
1-{2-[(4-aminophenyl)ethylamino]ethyl}-3-methyl-3H-imidazol-1-ium chloride;
N,N-bis[2-(3-methyl-3H-imidazol-1-ium)ethyl]-4-aminoaniline dichloride;
3-[2-(4-aminophenylamino)butyl]-1-methyl-3H-imidazol-1-ium chloride;
1-{[5-amino-2-(2-hydroxyethylamino)phenylcarbamoyl]-methyl}-3-methyl-3H-1-imidazol-1-ium chloride;
4-[2-(2,5-diaminophenoxy)ethyl]-1,3-dimethyl-3H-imidazol-1-ium bromide;
2-(2,5-diaminophenoxymethyl)-1,3-dimethyl-3H-imidazol-1-ium chloride;
4-[3-(4-aminophenylamino)propyl]-1,3-dimethyl-3H-imidazol-1-ium chloride;
4-[3-(4-amino-3-methylphenylamino)propyl]-1,3-dimethyl-3H-imidazol-1-ium chloride;
4-[(2,5-diaminophenylcarbamoyl)methyl]-1,3-dimethyl-3H-imidazol-1-ium chloride;
4-{2-[2-(2-amino-5-hydroxyphenyl)acetylamino]ethyl}-1,3-dimethyl-3H-imidazol-1-ium chloride;
4-[(5-amino-2-hydroxybenzylcarbamoyl)methyl]-1,3-dimethyl-3H-imidazol-1-ium chloride;

or an acid addition salt thereof.

8. A method of oxidation dyeing of keratin fibres, comprising the step of applying to said keratin fibres, a compound of formula (I) or an acid addition salt thereof as defined in claim 1, in an amount effective as an oxidation base.

9. A method according to claim 8, wherein said keratin fibres are human keratin fibres.

10. A method according to claim 9, wherein said human keratin fibres are hair.

11. A composition for the oxidation dyeing of human hair comprising, in a medium suitable for dyeing, at least one oxidation base selected from the compounds of formula (I) and acid addition salts thereof as defined in claim 1.

12. A composition according to claim 11, wherein said at least one oxidation base is present in an amount ranging from 0.0005 to 12% by weight relative to the total weight of the dye composition.

13. A composition according to claim 12, wherein said at least one oxidation base is present in an amount ranging from 0.005 to 6% by weight relative to the total weight of the dye composition.

14. A composition according to claim 11, wherein said medium suitable for dyeing comprises water or a mixture of water and at least one organic solvent selected from $C_1$–$C_4$ lower alkanols, glycerol, glycols and glycol ethers, and aromatic alcohols.

15. A composition according to claim 14, wherein said at least one organic solvent is selected from ethanol, isopropanol, 2-butoxyethanol, propylene glycol, propylene glycol monomethyl ether, diethylene glycol monoethyl ether, monomethyl ether, benzyl alcohol, and phenoxyethanol.

16. A composition according to claim 11, having pH of ranging from 3 to 12.

17. A composition according to claim 16, having pH of ranging from 5 to 11.

18. A composition according to claim 11, further comprising at least one additional oxidation base selected from para-phenylenediamines other than said at least one compound of formula (I), bis(phenyl)alkylenediamines, para-aminophenols other than said at least one compound of formula (I), ortho-aminophenols and heterocyclic bases other than said at least one compound of formula (I).

19. A composition according to claim 18, herein said at least one additional oxidation base is selected from para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl) para-phenylenediamine, N,N-bis(β-hydroxyethyl)para-phenylenediamine, 4-amino-N-(β-methoxyethyl)aniline, N,N-bis(β-hydroxyethyl)-N,N-bis(4-aminophenyl)-1,3-diaminopropanol, N,N-bis(β-hydroxyethyl)-N,N-bis(4-aminophenyl)ethylenediamine, N,N-bis(4-aminophenyl) tetramethylenediamine, N,N bis(β-hydroxyethyl)-N,N-bis (4-aminophenyl)tetramethylened amine, N,N-bis(4-methylaminophenyl)tetramethylenediamine and N,N-bis (ethyl)-N,N-bis(4-amino-3-methylphenyl)ethylenediamine, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4amino-2-methoxymethylphenol, 4-amino-2-aminomethylphenol and 4-amino-2-(hydroxyethylaminomethyl)phenol, 2-aminophenol, 2-amino-5-methylphenol, 2-amino-6-methylphenol, 5-acetamido-2-aminophenol, pyridine derivatives, pyrimidine derivatives and pyrazole derivatives.

20. A composition according to claim 19, wherein said at least one additional oxidation base is present in an amount ranging from 0.0005 to 12% by weight relative to the total weight of the dye composition.

21. A composition according to claim 20, wherein said at least one additional oxidation base is present in an amount ranging from 0.005 to 6% by weight relative to the total weight of the dye composition.

22. A composition according to claim 11, further comprising at least one coupler and/or at least one direct dye.

23. A composition according to claim 22, wherein said at least one coupler is selected from meta-phenylenediamines, meta-aminophenols, meta-diphenols and heterocyclic couplers, and acid addition salts thereof.

24. A composition according to claim 23, wherein said at least one coupler is selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and acid addition salts thereof.

25. A composition according to claim 22, wherein said at least one coupler is present in an amount ranging from 0.0001 to 10% by weight relative to the total weight of the dye composition.

26. A composition according to claim 25, wherein said at least one coupler is present in an amount ranging from 0.005 to 5% by weight relative to the total weight of the dye composition.

27. A composition according to claim 11, wherein said acid addition salt is selected from hydrochlorides, hydrobromides, sulphates, citrates, succinates, tartrates, lactates and acetates.

28. A method for dyeing keratin fibers, comprising the steps of applying said composition according to claim 11 to said keratin fibers and developing color at an acidic, neutral or alkaline pH with an oxidizing agent, said oxidizing agent being added to said composition at the time of applying to said keratin fibers, or said oxidizing agent being present in an oxidizing composition which is applied to said keratin fibers simultaneously or sequentially with said composition.

29. A method according to claim 28, wherein said oxidizing agent is selected from hydrogen peroxide, urea peroxide, alkali metal bromates and persalts.

30. A method according to claim 29, wherein said persalts are selected from perborates and persulphates.

31. A method according to claim 29, wherein said oxidizing agent is hydrogen peroxide.

32. A composition according to claim 11, in the form of a liquid, a cream, or a gel.

33. A multi-compartment dyeing device or kit for dyeing keratin fibers comprising at least two compartments, wherein, a first compartment comprises a dyeing composition according to claim 11, and a second compartment comprises an oxidizing composition.

34. A compound according to claim 1, wherein the number of unsaturated cationic groups Z of the formula (II) in said compound or acid addition salt thereof is at least equal to 1.

35. A composition according to claim 11, wherein said at least one oxidation base comprises at least one unsaturated cationic group Z of the formula (II).

36. A compound of formula (I) or an acid addition salt thereof:

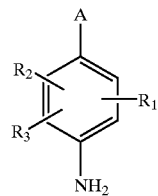

(1)

wherein:
$R_1$, $R_2$ and $R_3$, are identical or different and represent
a hydrogen atom;
a halogen atom;
a group Z;
a ($C_1$–$C_6$)alkylcarbonyl radical;
an amino($C_1$–$C_6$)alkylcarbonyl radical;
an N—Z-amino($C_1$–$C_6$)alkylcarbonyl radical;
an N—($C_1$–$C_6$)alkylamino($C_1$–$C_6$)alkylcarbonyl radical;
an N,N-di($C_1$–$C_6$)alkylamino($C_1$–$C_6$)alkylcarbonyl radical;
an amino($C_1$–$C_6$)alkylcarbonyl($C_1$–$C_6$)alkyl radical;
an N—Z-amino($C_1$–$C_6$)alkylcarbonyl($C_1$–$C_6$)alkyl radical;
an N—($C_1$–$C_6$)alkylamino($C_1$–$C_6$)alkylcarbonyl ($C_1$–$C_6$)alkyl radical;
an N,N-di($C_1$–$C_6$)alkylamino($C_1$–$C_6$)alkylcarbonyl ($C_1$–$C_6$)alkyl radical;
a carboxyl radical;
a ($C_1$–$C_6$)alkylcarboxyl radical;
a $C_1$–$C_6$ alkylsulphonyl radical;
an aminosulphonyl radical;
an N—Z-aminosulphonyl radical;
a $C_1$–$C_6$ N—alkylaminosulphonyl radical;
an N,N-di($C_1$–$C_6$)alkylaminosulphonyl radical;
an aminosulphonyl($C_1$–$C_6$)alkyl radical;
an N—Z-aminosulphonyl($C_1$–$C_6$)alkyl radical;
an N—($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a carbamyl radical;
an N—($C_1$–$C_6$)alkylcarbamyl radical;
an N,N-di($C_1$–$C_6$)alkylcarbamyl radical;
a carbamyl($C_1$–$C_6$)alkyl radical;
an N—($C_1$–$C_6$)alkylcarbamyl($C_1$–$C_6$)alkyl radical;
an N,N-di($C_1$–$C_6$)alkylcarbamyl($C_1$–$C_6$)alkyl radical;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
a trifluoro($C_1$–$C_6$)alkyl radical;
a cyano radical;
a group $OR_6$
a group $SR_6$;
an amino group protected with a ($C_1$–$C_6$)alkylcarbonyl, ($C_1$–$C_6$)alkylcarboxyl, trifluoro($C_1$–$C_6$) alkylcarbonyl, amino($C_1$–$C_6$)alkylcarbonyl, N—Z-amino($C_1$–$C_6$)alkylcarbonyl, N—($C_1$–$C_6$) alkylamino($C_1$–$C_6$)alkylcarbonyl, N,N-di($C_1$–$C_6$) alkylamino($C_1$–$C_6$)alkylcarbonyl, carbamyl, N—($C_1$–$C_6$)alkylcarbamyl, N,N-di($C_1$–$C_6$) alkylcarbamyl, $C_1$–$C_6$ alkylsulphonyl, aminosulphonyl, N—Z-amino-sulphonyl, $C_1$–$C_6$ N—alkylaminosulphonyl, N,N-di($C_1$–$C_6$) alkylaminosulphonyl, thiocarbamyl or formyl radical, or with a group Z;

an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_2$–$C_6$)alkyl, $C_1$–$C_6$ alkylcarbonyl, carbamyl, N—($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or with a group Z;

$R_6$ denotes
a $C_1$–$C_6$ alkyl radical;
a monohydroxy($C_1$–$C_6$)alkyl radical;
a polyhydroxy($C_2$–$C_6$)alkyl radical;
a group Z;
a ($C_1$–$C_6$)alkoxy($C_1$–$C_6$)alkyl radical;
an aryl radical;
a benzyl radical;
a carboxy($C_1$–$C_6$)alkyl radical;
a ($C_1$–$C_6$)alkylcarboxy($C_1$–$C_6$)alkyl radical;
a cyano($C_1$–$C_6$)alkyl radical;
a carbamyl($C_1$–$C_6$)alkyl radical;
an N—($C_1$–$C_6$)alkylcarbamyl($C_1$–$C_6$)alkyl radical;
an N,N-di($C_1$–$C_6$)alkylcarbamyl($C_1$–$C_6$)alkyl radical;
a trifluoro($C_1$–$C_6$)alkyl radical;
an aminosulphonyl($C_1$–$C_6$)alkyl radical;
an N—Z-aminosulphonyl($C_1$–$C_6$)alkyl radical;
an N—($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$)alkylcarboxyl, carbamyl, N—($C_1$–$C_6$)alkylcarbamyl, N,N-di($C_1$–$C_6$)alkylcarbamyl, thiocarbamyl and $C_1$–$C_6$ alkylsulphonyl radicals, and the group Z;

A represents a group —$NR_4R_5$ or a hydroxyl radical;

$R_4$ and $R_5$, are identical or different and represent
a hydrogen atom;
a group Z;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
an aryl radical;
a benzyl radical;
a cyano($C_1$–$C_6$)alkyl radical;
a carbamyl($C_1$–$C_6$)alkyl radical;
an N—($C_1$–$C_6$)alkylcarbamyl($C_1$–$C_6$)alkyl radical;
an N,N-di($C_1$–$C_6$)alkylcarbamyl($C_1$–$C_6$)alkyl radical;
a thiocarbamyl($C_1$–$C_6$)alkyl radical;
a trifluoro($C_1$–$C_6$)alkyl radical;
a sulpho($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
an aminosulphonyl($C_1$–$C_6$)alkyl radical;
an N—Z-aminosulphonyl($C_1$–$C_6$)alkyl radical;
an N—($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_2$–$C_6$)alkyl, ($C_1$–$C_6$)alkylcarbonyl, carbamyl, N—($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z is selected from the unsaturated cationic groups of formulae (II) and (III), and the saturated cationic groups of formula (IV):

$$\left[ -D - \underset{\underset{X^-}{}}{\overset{(R_{11})_x \quad (R_7)_y}{\underset{L—J}{N \overset{+}{\cdots} G}}} (R)_n \right] \quad (II)$$

$$\left[ -D - \underset{\underset{X^-}{}}{\overset{(R_{11})_x \quad (R_7)_y}{\underset{M—L—J}{N \overset{+}{\phantom{\cdots}} G}}} (R)_m \right] \quad (III)$$

$$\left[ -D - \underset{\underset{R_{10}}{}}{\overset{(R_{11})_x}{\underset{}{\overset{+}{N}—R_9}}} R_8 \right] X^- \quad (IV)$$

wherein:
D is a divalent linker arm which represents a linear or branched alkyl chain, said alkyl chain being uninterrupted or interrupted by at least one hetero atom, and said alkyl chain being unsubstituted or substituted with at least one hydroxyl or $C_1$–$C_6$ alkoxy radical, and said alkyl chain optionally having at least one ketone function;
the ring members E, G, J, L and M, are identical or different and represent a carbon, oxygen, sulphur or nitrogen atom;
n is an integer ranging from 0 and 4 inclusive;
m is an integer ranging from 0 and 5 inclusive;
the radicals R, are identical or different and represent
a group Z,
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a ($C_1$–$C_6$)alkylcarbonyl radical,
a thio radical,
a thio($C_1$–$C_6$)alkyl radical,
a $C_1$–$C_6$ alkylthio radical,
an amino radical,
an amino radical protected with a ($C_1$–$C_6$) alkylcarbonyl, carbamyl or $C_1$–$C_6$ alkylsuiphonyl radical;
a group NHR" or NR"R wherein R" and R, are identical or different and represent a $C_1$–$C_6$ alkyl radical, a monohydroxy($C_1$–$C_6$)alkyl radical or a polyhydroxy ($C_2$–$C_6$)alkyl radical;

$R_7$ represents
a $C_1$–$C_6$ alkyl radical,
a monohydroxy($C_1$–$C_6$)alkyl radical,
a polyhydroxy($C_2$–$C_6$)alkyl radical,
a cyano($C_1$–$C_6$)alkyl radical,
a tri($C_1$–$C_6$)alkylsilane($C_1$–$C_6$)alkyl radical,
a ($C_1$–$C_6$)alkoxy($C_1$–$C_6$)alkyl radical,
a carbamyl($C_1$–$C_6$)alkyl radical,
a ($C_1$–$C_6$)alkylcarboxy($C_1$–$C_6$)alkyl radical,
a benzyl radical or
a group Z of formula (II), (III) or (IV) as defined above;

$R_8$, $R_9$ and $R_{10}$, are identical or different and represent
a $C_1$–$C_6$ alkyl radical,
a monohydroxy($C_1$–$C_6$)alkyl radical,
a polyhydroxy($C_2$–$C_6$)alkyl radical,
a ($C_1$–$C_6$)alkoxy($C_1$–$C_6$)alkyl radical,
a cyano($C_1$–$C_6$)alkyl radical,
an aryl radical,
a benzyl radical,
an amido($C_1$–$C_6$)alkyl radical,
a tri($C_1$–$C_6$)alkylsilane($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
two of the radicals $R_8$, $R_9$ and $R_{10}$ can together form, with the nitrogen atom to which they are attached, a saturated 5- or 6-membered ring, wherein said ring may contain at least one additional hetero atom, and further wherein said ring is unsubstituted or substituted with:
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a keto($C_1$–$C_6$)alkyl radical,
a thio radical,
a thio($C_1$–$C_6$)alkyl radical,
a $C_1$–$C_6$ alkylthio radical,
an amino radical or
an amino radical protected with a ($C_1$–$C_6$) alkylcarbonyl, carbamyl or $C_1$–$C_6$ alkylsulphonyl radical;
one of the radicals $R_8$, $R_9$ and $R_{10}$ may represent a second group Z which is identical to or different from the first group Z;

$R_{11}$ represents
a $C_1$–$C_6$ alkyl radical;
a monohydroxy($C_1$–$C_6$)alkyl radical;
a polyhydroxy($C_2$–$C_6$)alkyl radical;
an aryl radical;
a benzyl radical;
an amino($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
a carboxy($C_1$–$C_6$)alkyl radical;
a cyano($C_1$–$C_6$)alkyl radical;
a carbamyl($C_1$–$C_6$)alkyl radical;
a trifluoro($C_1$–$C_6$)alkyl radical;
a tri($C_1$–$C_6$)alkylsilane($C_1$–$C_6$)alkyl radical;
a sulphonamido($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylketo($C_1$–$C_6$)alkyl radical;
an N—($C_1$–$C_6$)alkylcarbamyl($C_1$–$C_6$)alkyl radical;
an N—($C_1$–$C_6$)alkylsulphonamido($C_1$–$C_6$)alkyl radical;

x and y are integers equal to 0 or 1; with the proviso that:
in the unsaturated cationic groups of formula (II):
when x=0, the divalent linker arm D is attached to the nitrogen atom,
when x=1, the divalent linker arm D is attached to one of the ring members E, G, J or L,
y can take the value 1 only:
when the ring members E, G, J and L simultaneously represent a carbon atom and when the radical $R_7$ is borne by the nitrogen atom of the unsaturated ring; or
2) when at least one of the ring members E, G, J and L represents a nitrogen atom to which the radical $R_7$ is attached;
in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M represents a divalent atom and when the radical $R_7$ is borne by the nitrogen atom of the unsaturated ring;
in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of said saturated ring;

$X^-$ represents a monovalent or divalent anion; further with the provisos that:
the number of unsaturated cationic groups Z of formula (II) in said compound or acid addition salt thereof is at least equal to 1;
when A represents a group —$NR_4R_5$, wherein $R_4$ or $R_5$ represents a group Z wherein the divalent linker arm D represents an alkyl chain containing a ketone function, then said ketone function is not directly attached to the nitrogen atom of the group —$NR_4R_5$;
wherein 4-amino-3-methyl-N-ethyl-N-β-(1-pyridinium)ethylaniline chloride is excluded; and
when:
two of $R_1$, $R_2$ and $R_3$ are hydrogen atoms and one of $R_1$, $R_2$ and $R_3$ is a trifluoromethyl radical,
A is $NR_4R_5$, wherein:
one of $R_4$ and $R_5$ is chosen from a hydrogen atom and $C_1$–$C_4$ alkyl radicals, and
one of $R_4$ and $R_5$ is a group Z, wherein:
Z is a compound of formula (II), wherein:
D is chosen from $C_1$–$C_3$ alkyl chains, and
one of x, y and n is 1, and two of x, y, and n are 0, and
two of E, J, G and L are nitrogen atoms such that a 1,2,4-triazolium ring is formed,
then, $R_{11}$, $R_7$ and R, if present, are not $C_1$–$C_4$ alkyl radicals and $R_{11}$ and $R_7$ are not phenyl($C_1$–$C_2$) alkyl radicals.

* * * * *

UNITED STATES PATENT AND TRADEMARK OFFICE
CERTIFICATE OF CORRECTION

PATENT NO.      : 6,638,321 B1                                           Page 1 of 2
DATED           : October 28, 2003
INVENTOR(S)     : Alain Genet et al.

It is certified that error appears in the above-identified patent and that said Letters Patent is hereby corrected as shown below:

Title page,
Item [75], Inventors, "Aulay-sous-Bois" should read -- Aulnay-sous-Bois --.

Column 29,
Line 5, "(1)" should read -- (I) --.
Line 35, "alkylsuiphonyl" should read -- alkylsulphonyl --.

Column 30,
Line 20, "ary radical" should read -- aryl radical; --.
Line 21, "benzyl" should read -- a benzyl --.
Line 64, "delete "a" and the line of space.

Column 31,
Line 57, "group" should read -- a gourp --.

Column 32,
Line 38, "$R_1$" should read -- $R_{10}$ --.

Column 33,
Line 7, delete "p2" and insert a line break.
Line 27, after "nitrogen", delete the line break.
Line 30, "E G J or L," should read -- E, G, J or L, --.
Line 51, "$R_1$" should read -- $R_{10}$ --.
Line 61, "-$NP_4R_5$," should read -- -$NR_4R_5$, --.

Column 34,
Line 4, after "is a" insert -- group Z, --.

Column 35,
Line 37, "phenylcarbamoyl]-methyl}-3-methyl-3H-1-imidazol-" should read
-- phenylcarbamoyl]-mehtyl}-3-methyl-3H-imidazol- --.

Column 36,
Line 36, "N-(ß-hydroxypropyl)" should read -- N-(ß-hydroxypropyl)- --.
Line 37, "N,N-bis(ß-hydroxypropyl)para-" should read -- N,N-bis(ß-hydroxyethyl)-para- --
Lines 42-43, "N,N-bis(ß-hydroxyethyl)-N,N-bix(4-aminophenyl)tetramethylened amine," should read -- N,N-bis(ß-hydroxyethyl)-N,N-bis(4-aminophenyl) tetramethylenediamine, --.
Line 48, "4amino-2-" should read -- 4-amino-2- --.

UNITED STATES PATENT AND TRADEMARK OFFICE
CERTIFICATE OF CORRECTION

PATENT NO. : 6,638,321 B1
DATED : October 28, 2003
INVENTOR(S) : Alain Genet et al.

It is certified that error appears in the above-identified patent and that said Letters Patent is hereby corrected as shown below:

Column 38,
Line 1, "(1)" should read -- (I) --.
Line 24, "N-Z-amino($C_1$-$C_6$)alkylcarbonyl($C_1$ -$C_6$)alkyl" should read -- N-Z-amino($C_1$-$C_6$)alkylcarbonyl($C_1$-$C_6$)alkyl --

Column 39,
Lines 36-37, "trifluoro($C_1$ -$C_6$)alkylcarbonyl," should read -- trifluoro($C_1$-$C_6$) alkylcarbonyl, --.

Column 40,
Line 64, "alkylsuiphonyl" should read -- alkylsulphonyl --.

Column 42,
Line 7, "N-($C_1$-$C_6$)alkylcarbamyl($C_1$ -$C_6$)alkyl" should read -- N-($C_1$-$C_6$)alkylcarbamyl ($C_1$-$C_6$)alkyl --
Line 16, "when the" should read -- 1) when the --.

Signed and Sealed this

Thirtieth Day of March, 2004

JON W. DUDAS
*Acting Director of the United States Patent and Trademark Office*